(12) United States Patent
Purzner et al.

(10) Patent No.: US 10,213,449 B2
(45) Date of Patent: Feb. 26, 2019

(54) COMPOSITIONS AND METHODS FOR TREATING MEDULLOBLASTOMA

(71) Applicant: The Board of Trustees of the Leland Stanford Junior University, Stanford, CA (US)

(72) Inventors: Teresa Purzner, Stanford, CA (US); Matthew Peter Scott, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/617,543

(22) Filed: Jun. 8, 2017

(65) Prior Publication Data
US 2017/0360813 A1    Dec. 21, 2017

Related U.S. Application Data

(60) Provisional application No. 62/351,180, filed on Jun. 16, 2016.

(51) Int. Cl.
| | |
|---|---|
| *A61K 31/69* | (2006.01) |
| *A61K 31/122* | (2006.01) |
| *A61K 31/4192* | (2006.01) |
| *A61K 31/4745* | (2006.01) |
| *A61K 9/00* | (2006.01) |

(52) U.S. Cl.
CPC ............ *A61K 31/69* (2013.01); *A61K 9/0053* (2013.01); *A61K 31/122* (2013.01); *A61K 31/4192* (2013.01); *A61K 31/4745* (2013.01)

(58) Field of Classification Search
CPC .............. A61K 31/122; A61K 31/4192; A61K 31/4745; A61K 31/69; A61K 9/0053
See application file for complete search history.

(56) References Cited

U.S. PATENT DOCUMENTS

| 7,956,064 B2 | 6/2011 | Chua et al. | |
|---|---|---|---|
| 2004/0121968 A1 | 6/2004 | Ljubimov et al. | |
| 2010/0173013 A1* | 7/2010 | Drygin ................ | A61K 31/337 424/649 |

OTHER PUBLICATIONS

Agarwal (J Mol Genet Med, 8(1), p. 1-18, 2014).*
Shahi et al. (Oncology Reports, 681-688, 2008).*
Zheng (Clin Cancer Res 2013, 19(23), 6484-6494).*
Yoon et al. (Int J Cancer, 124, 109-119, 2009).*
Pagano et. al., "The selectivity of inhibitors of protein kinase CK2: an update.", Biochem J.,Nov. 1, 2008, pp. 353-365, 1;415(3), Biochemical Society, London, United Kingdom.
Cozza et. al., "The Selectivity of CK2 Inhibitor Quinalizarin: A Reevaluation", Biomed Res Int., 2015, pp. 1-9, vol. 2015, Article 734127, Hindawi Publishing Corporation, Cairo, Egypt.
Girardi et. al., "Different Persistence of the Cellular Effects Promoted by Protein Kinase CK2 Inhibitors CX-4945 and TDB", Biomed Res Int., 2015, pp. 1-9, vol. 2015, Article 185736, Hindawi Publishing Corporation, Cairo, Egypt.
Sarno et. al., "ATP site-directed inhibitors of protein kinase CK2: an update", Curr Top Med Chem., Jun. 2011, pp. 1340-1351, vol. 11, No. 11, Bentham Science Publishers, Emirate of Sharjah, United Arab Emirates.
Kieran, "Targeted treatment for sonic hedgehog-dependent medulloblastoma", Neuro Oncol., Aug. 2014, pp. 1037-1047, 16(8), Oxford University Press, Oxford, United Kingdom.
Litchfield, "Protein kinase CK2: structure, regulation and role in cellular decisions of life and death", Biochem J., Jan. 1, 2003, pp. 1-15, 369, Biochemical Society, London, United Kingdom.
Zhang et al., "Inhibition of CK2a Down-Regulates Hedgehog/Gli Signaling Leading to a Reduction of a Stem-Like Side Population in Human Lung Cancer Cells", PLoS One, Jun. 2012, pp. 1-10, vol. 7, Issue 6, e38996, PLoS One, San Francisco, CA.
Grizzi et al., "Antiangiogenic Strategies in Medulloblastoma: Reality or Mystery", Pediatr Res., May 2008, pp. 584-590, 63(5), Springer Nature, Victoria, Australia.
Zheng et al., "Targeting Protein Kinase CK2 Suppresses Prosurvival Signaling Pathways and Growth of Glioblastoma", Cancer Res., Dec. 1, 2013, pp. 6484-6494, 19(23), American Association for Cancer Research, Philadelphia, PA.
Jia et al., "Casein Kinase 2 Promotes Hedgehog Signaling by Regulating both Smoothened and Cubitus Interruptus", J Biol Chem., Nov. 26, 2010, pp. 37218-37226, 285(48), American Society for Biochemistry and Molecular Biology, Inc., Rockville, MD.
Berman et al, "Medulloblastoma Growth Inhibition by Hedgehog Pathway Blockade", Science, Aug. 30, 2002, pp. 1559-1561, 297(5586), American Association for the Advancement of Science, Washington, D.C.
Alexander et al., "Adult Glioblastoma", Journal of Clinical Oncology, Jun. 22, 2017, pp. 2402-2409, vol. 35, No. 21, American Society of Clinical Oncology, Alexandria, VA.

(Continued)

*Primary Examiner* — Umamaheswari Ramachandran
(74) *Attorney, Agent, or Firm* — Kyle A. Gurley; Bozicevic, Field & Francis LLP

(57) ABSTRACT

Provided are methods and compositions for treating an individual who has a medulloblastoma. Methods for treating an individual who has a medulloblastoma tumor can include a step of administering to the individual, at a dose sufficient to reduce the size and/or growth rate of the medulloblastoma tumor, a composition that includes a casein kinase II (CK2) inhibitor (e.g., a CK2-selective inhibitor such as CX-4945). In some cases, the medulloblastoma tumor is a hedgehog-dependent medulloblastoma tumor. In some cases, the medulloblastoma tumor is a hedgehog-independent medulloblastoma tumor. In some cases, the medulloblastoma tumor is smoothened inhibitor-resistant (SMO inhibitor-resistant). In some cases, the medulloblastoma is resistant to treatment with 4,5,6,7-tetrabromo-2H-benzotriazole (TBB). In some cases, the dose is sufficient to cause long term regression of the medulloblastoma tumor, and in some cases, the dose is sufficient to increase the chance of survival of the individual.

14 Claims, 16 Drawing Sheets
(16 of 16 Drawing Sheet(s) Filed in Color)
Specification includes a Sequence Listing.

(56) References Cited

OTHER PUBLICATIONS

Alexandrov et al., "Signatures of mutational processes in human cancer", Nature, Aug. 22, 2013, pp. 415-421, vol. 500, Macmillan Publishers Limited, Basingstoke, United Kingdom.

Cancer Genome Atlas Research Network, "Comprehensive genomic characterization defines human glioblastoma genes and core pathways", Nature, Oct. 23, 2008, pp. 1061-1068, vol. 455, Macmillan Publishers Limited, Basingstoke, United Kingdom.

Jones et al., "Dissecting the genomic complexity underlying medulloblastoma", Nature, Aug. 2, 2012, pp. 100-105, 488, Macmillan Publishers Limited, Basingstoke, United Kingdom.

Lorusso et al., "Phase I Trial of Hedgehog Pathway Inhibitor Vismodegib (GDC-0449) in Patients with Refractory, Locally Advanced or Metastatic Solid Tumors", Clinical Cancer Research, Feb. 7, 2011, pp. 1-11, American Association for Cancer Research, Philadelphia, PA.

Northcott et al., "Subgroup-specific structural variation across 1,000 medulloblastoma genomes", Nature, Aug. 2, 2012, pp. 49-56, vol. 488, Macmillan Publishers Limited, Basingstoke, United Kingdom.

Ostrom et al., "CBTRUS Statistical Report: Primary Brain and Central Nervous System Tumors Diagnosed in the United States in 2008-2012", Neuro Oncol., Oct. 2015, pp. iv1-iv62, Suppl 4, Oxford University Press, Oxford, United Kingdom.

Parsons et al., "An Integrated Genomic Analysis of Human Glioblastoma Multiforme", Science, Sep. 26, 2008, pp. 1-15, vol. 321, Issue 5897, American Association for the Advancement of Science, Washington, D.C.

Rudin et al., "Treatment of Medulloblastoma with Hedgehog Pathway Inhibitor GDC-0449", The New England Journal of Medicine, Sep. 17, 2009, p. 1173-1178, 361, Massachusetts Medical Society, Waltham, MA.

Sloan et al., "Targeting Glioma Initiating Cells in GBM: ABTC-0904, A Randomized Phase 0/II Study Targeting the Sonic Hedgehog-Signaling Pathway", Neuro-Oncology, Jul. 23, 2014, p. 2026, 32, No. 15, Oxford University Press, Oxford, United Kingdom.

Tang et al., "Gene mutation profiling of primary glioblastoma through multiple tumor biopsy guided by H-magnetic resonance spectroscopy", Int J Clin Exp Pathol., May 1, 2015, 5327-5335, 8(5), National Center for Biotechnology Information, Bethesda MD.

Taylor et al., "Molecular subgroups of medulloblastoma: the current consensus", Acta Neuropathol., Apr. 2012, pp. 465-472, vol. 123, Issue 4, Springer Nature, Basel, Switzerland.

* cited by examiner

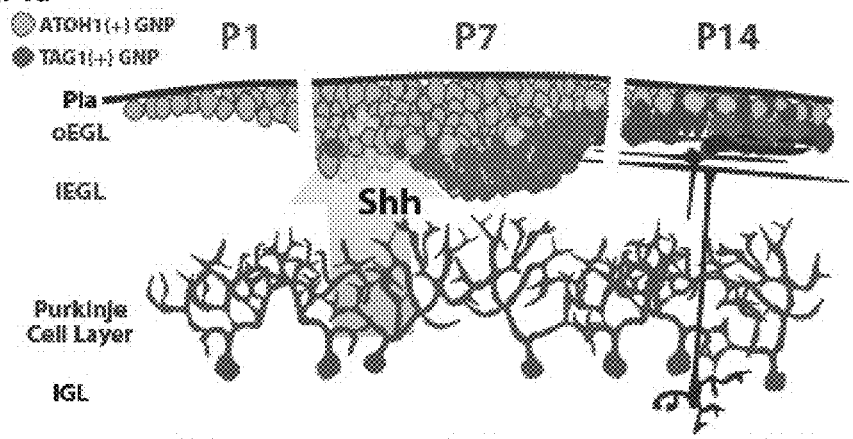
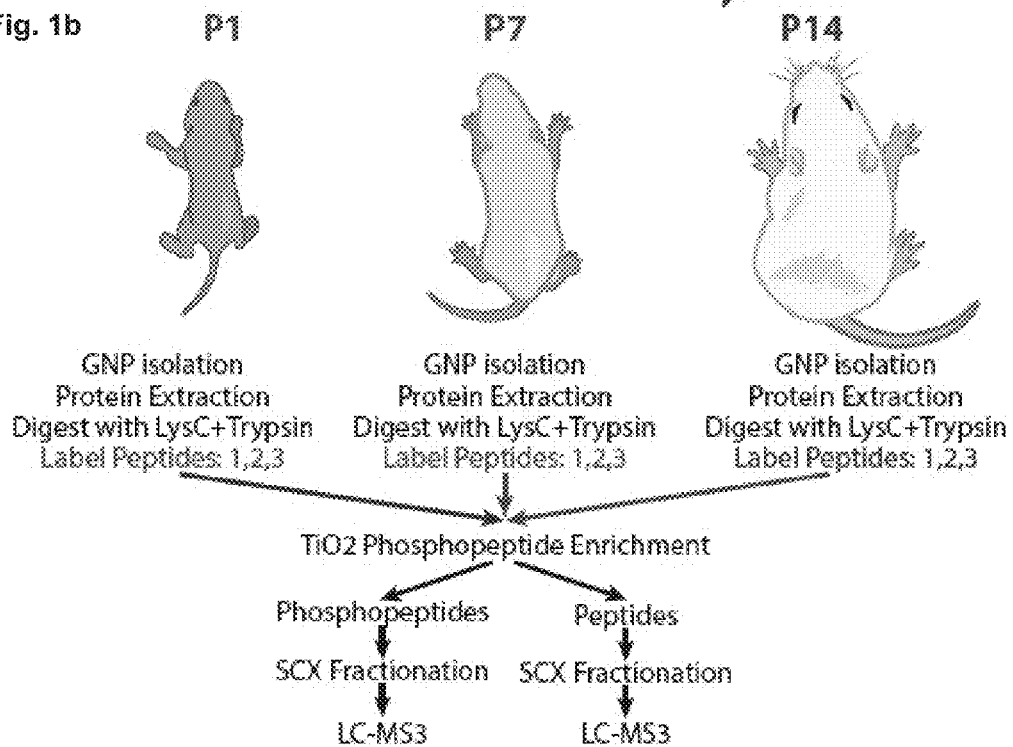

COMPOSITIONS AND METHODS FOR TREATING MEDULLOBLASTOMA

CROSS-REFERENCE

This application claims the benefit of U.S. Provisional Patent Application No. 62/351,180 filed Jun. 16, 2016, which application is incorporated herein by reference in its entirety.

INTRODUCTION

One limitation of targeted cancer therapy is the molecular heterogeneity found between tumors and within a tumor over time. This makes it challenging to create therapeutics that have long-term effect in many patients. As with many tumors, medulloblastomas "hijack" cellular signaling, and cells—in this case granule neuron precursors (GNPs)—are driven to unrestrained proliferation.

There is a need in the art for compositions and methods to treat individuals who have medulloblastoma.

SUMMARY

Methods and compositions are provided for treating an individual who has a medulloblastoma. Methods for treating an individual who has a medulloblastoma tumor can include a step of administering to the individual, at a dose sufficient to reduce the size and/or growth rate of the medulloblastoma tumor, a composition that includes a casein kinase II (CK2) inhibitor. In some cases, the medulloblastoma tumor is a hedgehog-dependent medulloblastoma tumor. In some cases, the medulloblastoma tumor is a hedgehog-independent medulloblastoma tumor. In some cases, the medulloblastoma tumor is smoothened inhibitor-resistant (SMO inhibitor-resistant). In some cases, the medulloblastoma is resistant to treatment with 4,5,6,7-tetrabromo-2H-benzotriazole (TBB). In some cases, the dose is sufficient to cause long term regression of the medulloblastoma tumor, and in some cases, the dose is sufficient to increase the chance of survival of the individual.

In some embodiments, composition (which includes a CK2 inhibitor) includes a CK2-selective inhibitor (i.e., in some cases the CK2 inhibitor is a CK2-selective inhibitor). In some cases, the CK2-selective inhibitor is selected from: 5-(3-Chloroanilino)benzo[c][2,6]naphthyridine-8-carboxylic acid (CX-4945), 1,2,5,8-tetrahydroxyanthraquinone (quinalizarin), 4,5,6,7-tetrabromo-2H-benzotriazole (TBB), and 1-hydroxy-6-methyl-2-propylsulfonylthieno[3,2-d]diazaborinine (TDB). In some cases, the CK2-selective inhibitor is CX-4945. In some cases, the CK2-selective inhibitor is TBB. In some cases, the CK2-selective inhibitor is quinalizarin. In some cases, the CK2-selective inhibitor is TDB.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1a-1f. Quantitative mapping of the proteome and phosphoproteome during GNP development. (FIG. 1a) GNPs originate in the outer EGL (P1) and undergo multiple rounds of proliferation (P7) prior to exiting the cell cycle (P14) in the inner EGL (dark red). Following neurite extension, early granule neurons migrate through the molecular layer and purkinje cell layer prior to fully maturing into a dendritic granule neuron. (FIG. 1b) Experimental approach: GNPs were isolated at postnatal days 1, 7 and 14 (P1, P7, P14) in biological triplicate. Proteins were extracted, digested and labeled with 9 unique TMT tags. Equal quantities of tagged peptides were mixed and phosphopeptides enriched using TiO2. Peptides and phosphopeptides were fractionated using SCX. Protein ID, abundance and phosphorylation state were determined via HPLC-MS/MS/MS. (FIG. 1c) Undirected hierarchical clustering of proteomic samples demonstrates strong correlation between biological replicates and relative similarity between MB and proliferative GNPs (P7). P14 (terminally differentiating) GNPs negatively correlate with proliferative GNPs. (FIG. 1d) Weighted venn diagrams demonstrate overlap between >1.5-fold changing protines at the two transition points (P1:P7, P7:P14). Distribution of relative peptide expression. Dotted lines represent 95% of peptides. (FIG. 1e) Gene sets enrichment analysis of GO terms in the 1.5-fold changing proteins between developmental stages and MB demonstrates similarities (cell cycle regulation) and differences (biosynthesis vs. neurogenesis) between P1 and P7 GNPs, while proteins in P14 GNPs are enriched for polarity, axonogenesis and migration associated terms. Red asterisks denote expression of specific cell cycle regulators and markers of differentiation that are represented in FIG. 1f.

(FIG. 2a) Undirected hierarchical clustering of proteomic samples demonstrates strong correlation between biological replicates and relative similarity between MB and proliferative GNPs (P7). P14 (terminally differentiating). Relative distribution of phosphopeptides. Dotted lines represent 95% of prhosphopeptides. GNPs negatively correlate with proliferative GNPs. (FIG. 2b) relative protein vs phosphorylation expression. Red dots represent top 5% of changing phosphopeptides. (FIG. 2c) Phosphomotif analysis of 1.5-fold changing events demonstrates enrichment of 16 motifs including known regulators of GNP development such as PKA, TGFBR1, and CDKs (FIG. 2b) and substantial representation of CK2 motifs (FIG. 2c). (FIG. 2d) Motif-driving genes include known (*) and uncharacterized CK2 substrates. (Top to Bottom: SEQ ID NOs.: 1-22) (FIG. 2e) schematic of CK2 inhibitor injections in wildtype mice between P3 and P7. (FIG. 2f) Relative cerebellar size of wildtype vs. CK2 inhibitor treated mice. (FIG. 2g) relative abundance of proliferating GNPs (Atoh1), differentiating GNPs (tag1) and apoptosis (TUNNEL).

(FIG. 3a) schematic of the canonical hedgehog signaling pathway. NIH 3T3 cells exposed to Shh show loss of Gli1 induction following (FIG. 3b) Csnk2a1 knockdown and (FIG. 3c) in cells treated with CK2 inhibitors, TBB and CX-4945, or SMO inhibitor, GDC-0449. NIH3T3's treated with SMO agonist SAF (FIG. 3d), Sufu−/− MEFs (FIG. 3e) and NIH3T3s with constitutively active Gli (FIG. 3O show dose dependent loss of Gli1 expression following treatment with TBB. (FIG. 3g) Endogenous Gli2 demonstrates decreased stability as a result of CK2 inhibition however CMV-drive expression of Gli2deltaN shows no significant decrease in expression.

(FIG. 4a) CK2 inhibitors TBB (left) and CX-4945 (right) show dose dependent tumoricidal effects in 4 different MB cell lines derived from primary MB generated in Ptch−/− mice. (FIG. 4b) Schematic for in vivo studies. (FIG. 4c) Mice harboring Ptch+/−; Trp53−/− MB flank allografts were treated with TBB show decreased growth relative to vehicle control. (FIG. 4d) Mice harboring flank MB allografts derived from MB generated in Ptch+/−; Tpr53−/−; SmoD477G were treated with TBB, GDC-0449, or vehicle control. Note, tumors derived from these mice are resistant to vismodegib, and TBB treated mice showed significant response over control and GDC-0449 treated mice. (FIG. 4e) Decreased BrdU incorporation (red) in flank allografts following TBB administration relative to GDC-0449 and control treated mouse. DAPI counterstain in blue. (FIG. 4f) Kaplan-Meier survival analysis of mice harboring intracranial allografts of Ptch+/−; Trp53−/−; SmoD477G MBs treated with CX-4945 and vehicle control. (FIG. 4g) Kaplan-Meier analysis of CK2 expression and overall survival in SHH subtype MB. High CK2 expression as measured by gene expression microarray analysis correlates with decreased overall survival in patients with SHH subtype MBs.

DETAILED DESCRIPTION

Figure 1C:
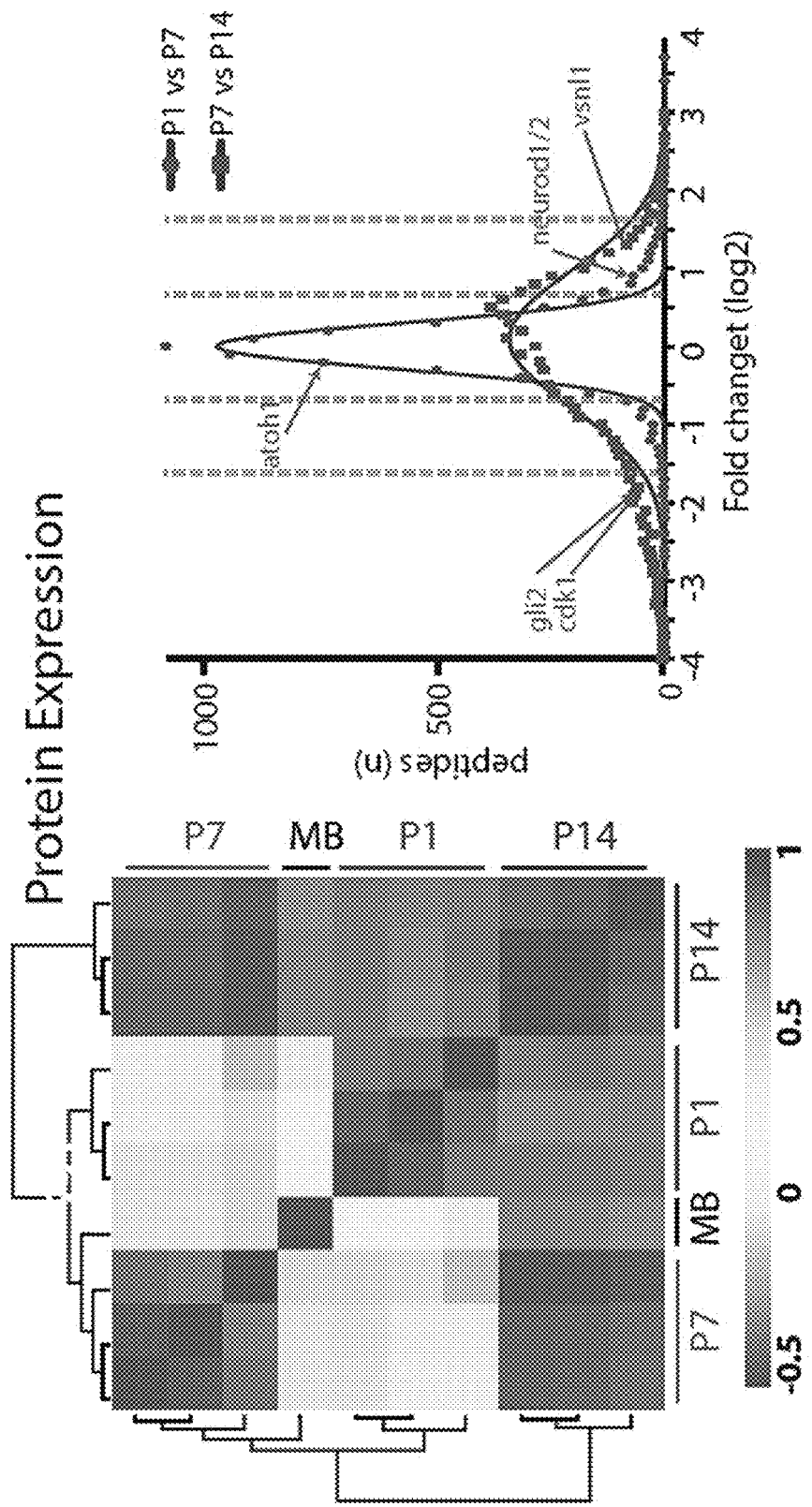

Methods and compositions are provided for treating an individual who has a medulloblastoma. Methods for treating an individual who has a medulloblastoma tumor can include a step of administering to the individual, at a dose sufficient to reduce the size and/or growth rate of the medulloblastoma tumor, a composition that includes a casein kinase II (CK2) inhibitor. In some cases, the medulloblastoma tumor is a hedgehog-dependent medulloblastoma tumor. In some cases, the medulloblastoma tumor is a hedgehog-independent medulloblastoma tumor. In some cases, the medulloblastoma tumor is smoothened inhibitor-resistant (SMO inhibitor-resistant). In some cases, the medulloblastoma is resistant to treatment with 4,5,6,7-tetrabromo-2H-benzotriazole (TBB). In some cases, the dose is sufficient to cause long term regression of the medulloblastoma tumor, and in some cases, the dose is sufficient to increase the chance of survival of the individual.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "recipient", "individual", "subject", "host", and "patient", are used interchangeably herein and refer to any mammalian subject for whom diagnosis, treatment, or therapy is desired (e.g., mice, non-human primates, humans, etc.). "Mammal" for purposes of treatment refers to any animal classified as a mammal, including humans, non-human primates, domestic and farm animals, and zoo, sports, or pet animals, such as dogs, horses, cats, cows, sheep, goats, pigs, etc. In some cases, an individual of a subject method is a mammal. In some embodiments, the mammal is a rodent (e.g., a rat, a mouse), in some cases the mammal is a non-human primate, and in some cases the mammal is a human.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc.

The term "biological sample" encompasses a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell (e.g., cancer cell) from a patient can also include non-inflicted cells. In some cases, a biological sample is a biopsy sample (e.g., a biopsy of an MB tumor).

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides/epitopes). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

Compositions and Methods

Provided are compositions and methods for treatment of an individual who has a Medulloblastoma (i.e., an individual who has a medulloblastoma tumor). In some embodiments, a subject method is a method of treating an individual who has a medulloblastoma tumor, and the method includes a step administering a composition that includes a casein kinase II (CK2) inhibitor (e.g., a CK2-selective inhibitor) to the individual at a dose sufficient to reduce the size and/or growth rate of the medulloblastoma tumor.

Medulloblastoma and Hedgehog (Hh)

Molecular studies have identified pathways involved in the tumorigenesis of many cancers including medulloblastoma (MB), the most common malignant brain tumor in young children (e.g., see Kieran et. al., Neuro Oncol. 2014 August; 16(8):1037-47, Epub 2014 Jun. 20). The hedgehog (Hh) pathway was implicated in MB when germline mutations in patched (PTCH) were detected in patients with Gorlin syndrome, a heritable condition associated with an increased risk of MB and other cancers including basal cell carcinoma (BCC). Since then, profiling studies and other genetic analyses have confirmed the involvement of the Hh pathway in the pathogenesis of MB and BCC. In addition, inhibitors of the Hh pathway have demonstrated efficacy in MB and BCC.

The 4 major histological variants of MB according to the World Health Organization include classical, desmoplastic/nodular, MB with extensive nodularity, and anaplastic/large cell. Efforts to differentiate MB have shifted from histological to molecular classification. A consensus, based on gene expression profiling data from several independent laboratories, reports 4 molecular subgroups of MB: wingless (WNT; group 1), sonic hedgehog (SHH; group 2—also referred to herein as Hh dependent), group 3 (v-myc avian myelocytomatosis viral oncogene homolog [MYC] amplified), and group 4 (see e.g., Taylor et. al., Acta Neuropathol. 2012 April; 123(4):465-72, Epub 2011 Dec. 2).

In some cases, an individual being treated using a subject method (e.g., using a composition that includes a CK2 inhibitor, e.g., a CK2-selective inhibitor such as CX-4945 and/or TBB) has a Hh dependent MB tumor (i.e., an MB of group 2). In some cases, an individual being treated using a subject method (e.g., using a composition that includes a CK2 inhibitor, e.g., a CK2-selective inhibitor such as CX-4945 and/or TBB) has a Hh independent MB tumor (i.e., a non-hedgehog dependent, i.e., an MB that is not of group 2, i.e., an MB that is of group 1, 3, or 4). In some cases, an individual being treated using a subject method (e.g., using a composition that includes a CK2 inhibitor, e.g., a CK2-selective inhibitor such as CX-4945 and/or TBB) has a group 1 MB tumor. In some cases, an individual being treated using a subject method (e.g., using a composition that includes a CK2 inhibitor, e.g., a CK2-selective inhibitor such as CX-4945 and/or TBB) has a group 3 MB tumor. In some cases, an individual being treated using a subject method (e.g., using a composition that includes a CK2 inhibitor, e.g., a CK2-selective inhibitor such as CX-4945 and/or TBB) has a group 4 MB tumor.

The SHH group (also referred to herein as hedgehog dependent medulloblastoma (MB) or Hh-driven MB) is characterized by activated hedgehog (Hh) pathway signaling. The Hh pathway is important for cell proliferation, differentiation, and survival during embryonic and fetal development and later, during postnatal development and adulthood, plays a role in bone development, stem cell maintenance, and maintenance and repair of some tissues. Hh signaling is initiated when a Hh ligand (e.g., SHH, Indian hedgehog, desert hedgehog) binds to the transmembrane receptor PTCH, releasing its inhibition of the signal transducer smoothened (SMO). Activation of SMO initiates downstream signaling events, including release of glioma-associated oncogene (GU) transcription factors from suppressor of fused (SUFU), a negative regulator of the pathway, allowing GLIs to translocate to the nucleus and induce expression of Hh pathway target genes. Aberrant expression of Hh-target genes leads to excessive cell proliferation and tumorigenesis. SHH signaling, which normally stimulates the proliferation of lineage-restricted cerebellar granule neuron precursors (CGNPs) during cerebellar development, can lead to MB formation when aberrantly activated. Mutations in PTCH and SUFU have been identified in up to 17% and 10% of MBs, respectively. Amplification of GLI2 has also been identified in MB.

Preclinical studies have identified a role for the Hh pathway in the tumorigenesis of MB and demonstrated that inhibition of the Hh pathway impedes tumor growth. In mouse models, treatment with inhibitors of SMO, the positive regulator of the Hh signaling pathway, leads to reduced tumor growth and increased survival. SMO inhibitors include but are not limited to HhAntag, N-[(3R,3'R,3'aS, 4aR,6'S,6aR,6bS,7'aR,9S,12aS,12bS)-3',6',11,12b-tetramethylspiro[1,2,3,4,4a,5,6,6a,6b,7,8,10,12,12a-tetradecahydronaphtho[2,1-a]azulene-9,2'-3a,4,5,6,7,7a-hexahydro-3H-furo[3,2-b]pyridine]-3-yl]methanesulfonamide (saridegib) (IPI-926), 1-[4-[5-chloro-4-(3,5-dimethylpyridin-2-yl) pyridin-2-yl]piperazin-1-yl]-3-methylsulfonylpropan-1-one (PF-5274857), cyclopamine, and 4-fluoro-N-methyl-N-[1-[4-(2-methylpyrazol-3-yl)phthalazin-1-yl]piperidin-4-yl]-2-(trifluoromethyl)benzamide (LY2940680), 2-chloro-N-(4-chloro-3-pyridin-2-ylphenyl)-4-methylsulfonylbenzamide (vismodegib)(GDC-0449).

However, because of resistance and the presence of mutations downstream of SMO, not all patients with Hh dependent MB respond to SMO inhibitors. Thus, in some cases, an MB (e.g., a Hh dependent MB) is resistant to treatment with a SMO inhibitor. In other words, a medulloblastoma tumor can be smoothened (SMO) inhibitor-resistant (i.e., a SMO inhibitor-resistant MB tumor). Resistance to SMO inhibitors has been observed in preclinical MB mouse models and in at least 1 patient with MB in the clinic. The observed resistance has been attributed to acquired mutations in SMO (L225R, N223D, S391N, D338N, D477G [D473H in human SMO], G457S, and E518), amplification of GL12, MYCN, and cyclin D1, upregulation of the IGF-1R-PI3K pathway (SUFU and PTEN are closely linked on chromosome 10), and upregulation of the adenosine triphosphate-binding cassette transporter p-glycoprotein substrate, which is a common mechanism of drug resistance in cancer cells. In addition, a truncated version of GLI1, identified in MB cells, was shown to regulate anchorage-independent growth and morphology and rendered MB cells resistant to the SMO inhibitors cyclopamine and vismodegib.

In some cases, a SMO inhibitor-resistant MB can nonetheless be treated with a subject composition (e.g., one that includes a CK2 inhibitor, e.g., a CK2-selective inhibitor such as CX-4945 and/or TBB). Thus in some cases, an individual being treated using a subject method has a SMO inhibitor-resistant MB tumor. In some cases, an individual being treated using a subject method (e.g., using a composition that includes a CK2 inhibitor, e.g., a CK2-selective inhibitor such as CX-4945 and/or TBB) has a Hh independent MB (e.g., an MB that is not associated with increased Hh signaling). For example, in some cases, an individual being treated using a subject method (e.g., using a composition that includes a CK2 inhibitor, e.g., a CK2-selective inhibitor such as CX-4945 and/or TBB) has a group 1, 3, or 4 MB. In some cases, the individual has a group 1 MB, in some cases the individual has a group 3 MB, and in some cases the individual has a group 4 MB.

CK2 Inhibitors

As noted above, provided are methods that include a step of administering a composition to an individual with an MB tumor, where the composition includes a casein kinase II (CK2) inhibitor (e.g., a CK2-selective inhibitor). Casein kinase II (CK2) is a serine/threonine protein kinase that phosphorylates acidic proteins such as casein. CK2 can exists as a tetramer and can be composed of an alpha, an alpha-prime, and two beta subunits. The alpha subunits can contain the catalytic activity while the beta subunits can undergo autophosphorylation. CK2 inhibitors are compounds that inhibit the activity of CK2.

Some CK2 inhibitors inhibit other kinases in addition to CK2 (in some cases they inhibit other kinases just as well if not better than CK2), and are sometimes referred to as promiscuous CK2 inhibitors. In some cases, a CK2 inhibitor is a "CK2-selective" inhibitor, in which case the inhibitor selectively inhibits the activity of CK2 (relative to other kinases). While there is a range of selectivity among CK2-selective inhibitors (e.g., some are more selective than others, and a CK2-selective inhibitor need not be so selective that CK2 is the only kinase that it inhibits), one of ordinary skill in the art will be readily able to determine (e.g., using the examples in the following paragraphs) whether a given CK2 inhibitor is a selective inhibitor. In some cases, a CK2-selective inhibitor has a Promiscuity Score (PS) of 48% or lower. A "Promiscuity Score" (PS) expresses the average inhibition of all the kinases of a tested panel by a concentration of the inhibitor sufficient to inhibit the kinase under consideration by around 90% (e.g., see Sarno et. al., Curr Top Med Chem. 2011; 11(11):1340-51). In some cases, the CK2-selective inhibitor has a PS of 40% or lower (e.g., 35% or lower, 30% or lower, 25% or lower, or 20% or lower).

Examples of CK2 inhibitors (compounds known to inhibit CK2) include, but are not limited to: 4,5,6,7-tetrabromo-2H-benzotriazole (TBB), 4,5,6,7-tetrabromo-1H-benzimidazole (TBI, TBBz, K17), 2-dimethylamino-4,5,6,7-tetrabromo-1H-benzimidazole (DMAT), 5-(3-chloroanilino)benzo[c][2,6]naphthyridine-8-carboxylic acid (CX-4945, Silmitasertib), 1,2,5,8-tetrahydroxyanthraquinone (quinalizarin), 1-hydroxy-6-methyl-2-propylsulfonylthieno[3,2-d]diazaborinine (TDB, K164), 2-(3,4-dihydroxyphenyl)-3,5,7-trihydroxychromen-4-one (quercetin), (E)-3-(2,3,4,5-tetrabromophenyl)prop-2-enoic acid (TBCA), Ellagic Acid, 4,5,6,7-tetraiodo-1H-benzimidazole (TIBI), 5,7-dihydroxy-2-(4-hydroxyphenyl)chromen-4-one (apigenin), 1,3,8-trihydroxy-6-methylanthracene-9,10-dione (emodin), 5,6-dichloro-1-β-D-ribofuranosylbenzimidazole (DRB), NBC (for structure see Sarno et. al., Curr Top Med Chem. 2011; 11(11):1340-51), MNX (for structure see Sarno et. al., Curr Top Med Chem. 2011; 11(11):1340-51), MNA (for structure see Sarno et. al., Curr Top Med Chem. 2011; 11(11):1340-51), and K36, K59, K60, K62, K64, K66, K74 and K75. For information on K36, K59, K60, K62, K64, K66, K74 and K75, see, e.g., Pagano et. al., Biochem J. 2008 Nov. 1; 415(3):353-65 (structures are depicted below).

Examples of "CK2-selective" inhibitors can include, but are not limited to: CX-4945, TBB, TBCA, quinalizarin, TDB, TIBI, Ellagic Acid, NBC, MNX, MNA, K36, K59, K60, K62, K64, K66, K74 and K75. For more information regarding the relative selectivity of CK2 inhibitors (see e.g., Pagano et. al., Biochem J. 2008 Nov. 1; 415(3):353-65; Cozza et. al., Biomed Res Int. 2015; 2015:734127, Epub 2015 Oct. 19; Girardi et. al., Biomed Res Int. 2015; 2015: 185736, Epub 2015 Oct. 19; Cozza et al., Biochim Biophys Acta. 2013 July; 1834(7):1402-9, Epub 2013 Jan. 27; and Sarno et. al., Curr Top Med Chem. 2011; 11(11):1340-51). Structures are provided here for some, but not all, of the CK2-inhibitors described above.

CX-4945

5-(3-Chloroanilino)benzo[c][2,6]naphthyridine-8-carboxylic acid (also known as Silmitasertib)

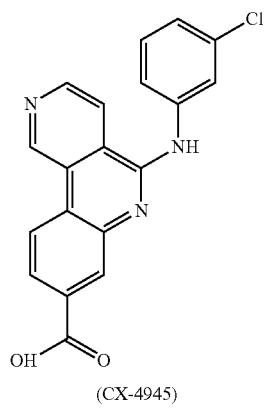 [SMILES: O=C(O)c1ccc2c(c1)nc(Nc1cccc(Cl)c1)c1ccncc12]

(CX-4945)

TBB 4,5,6,7-tetrabromo-2H-benzotriazole (also known as
4,5,6,7-tetrabromo-2-azabenzimidazole; 4,5,6,7-
tetrabromobenzotriazole; 4,5,6,7-Tetrabromo-1H-
benzotriazole; NSC 231634; and 17374-26-4)

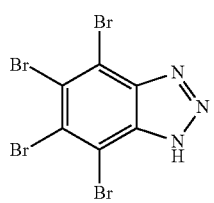

(TBB)

K36

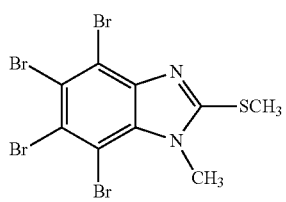

(K36)

K59

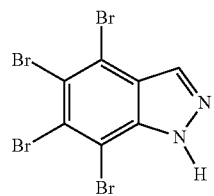

(K59)

K60

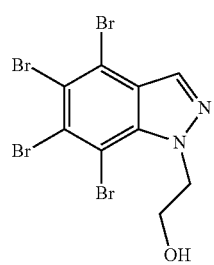

(K60)

K62

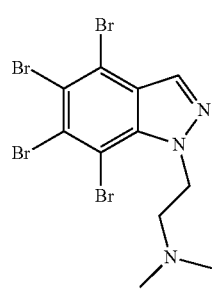

(K62)

K64

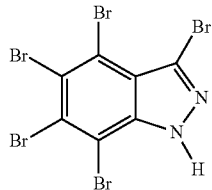

(K64)

K66

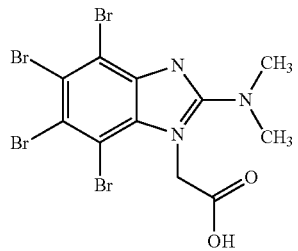

(K66)

K74

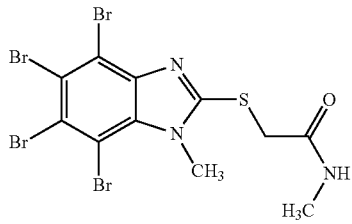

(74)

K75

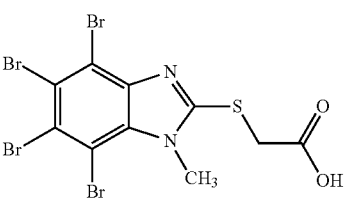

(K75)

In some cases, a CK2 inhibitor (e.g., a CK2-selective inhibitor) of a subject composition and/or method (e.g., for treating an individual who has an MB tumor) is selected from CX-4945, TBB, TBCA, quinalizarin, TDB, TIBI, Ellagic Acid, NBC, MNX, MNA, K36, K59, K60, K62, K64, K66, K74 and K75. In some cases, the CK2 inhibitor (e.g., a CK2-selective inhibitor) is selected from CX-4945, TBB, quinalizarin, TBCA, TIBI, Ellagic Acid, K66, MNA, K59, and TBB. In some cases, the CK2 inhibitor (e.g., a CK2-selective inhibitor) is selected from CX-4945, TBB, and quinalizarin. In some cases, the CK2 inhibitor (e.g., a CK2-selective inhibitor) is selected from CX-4945 and TBB. In some cases, the CK2 inhibitor (e.g., a CK2-selective inhibitor) is selected from CX-4945 and quinalizarin.

In some cases, the CK2 inhibitor (e.g., a CK2-selective inhibitor) of a subject composition and/or method (e.g., for treating an individual who has an MB tumor) is CX-4945. In some cases, the CK2 inhibitor (e.g., a CK2-selective inhibitor) is TBB. In some cases, the CK2 inhibitor (e.g., a CK2-selective inhibitor) is quinalizarin.

In some cases, the CK2 inhibitor of a subject composition and/or method is a CK2-selective inhibitor (e.g., CX-4945) other than TBB. In some cases, the individual being treated has an MB tumor that is resistant to treatment with TBB (i.e., an MB tumor that is resistant to TBB).

Formulations

A CK2 inhibitor (e.g., any CK2 inhibitor above, a CK2-selective inhibitor, e.g., CX-4945, etc.) can be prepared as a dosage unit, with a pharmaceutically acceptable excipient, with pharmaceutically acceptable salts and esters, etc. Compositions can be provided as pharmaceutical compositions.

Pharmaceutical Compositions.

A suitable CK2 inhibitor (e.g., any CK2 inhibitor above, a CK2-selective inhibitor, e.g., CX-4945, etc.) can be provided in pharmaceutical compositions suitable for therapeutic use, e.g. for human treatment. In some embodiments, pharmaceutical compositions of the present disclosure include one or more therapeutic entities of the present disclosure (e.g., one or more CK2 inhibitors) and can include a pharmaceutically acceptable carrier, a pharmaceutically acceptable salt, a pharmaceutically acceptable excipient, and/or esters or solvates thereof. In some embodiments, the use of a CK2 inhibitor includes use in combination with (co-administration with) another therapeutic agent (e.g., another agent for preventing or treating cancer such as medulloblastoma). Therapeutic formulations comprising a CK2 inhibitor can be prepared by mixing the agent(s) having the desired degree of purity with a physiologically acceptable carrier, a pharmaceutically acceptable salt, an excipient, and/or a stabilizer (Remington's Pharmaceutical Sciences 16th edition, Osol, A. Ed. (1980)) (e.g., in the form of lyophilized formulations or aqueous solutions). A composition having a CK2 inhibitor can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this disclosure can be present in unsalified or unesterified form, or in salified and/or esterified form, and the naming of such compounds is intended to include both the original (unsalified and unesterified) compound and its pharmaceutically acceptable salts and esters.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

The terms "treatment", "treating", "treat" and the like are used herein to generally refer to obtaining a desired pharmacologic and/or physiologic effect (e.g., reducing tumor size, stabilizing a tumor, reducing the growth rate of a tumor, reducing the number of cancer cells present, and the like). The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment can include those already inflicted (e.g., those with an MB tumor) as well as those in which prevention is desired (e.g., those with increased susceptibility to cancer).

A therapeutic treatment is one in which the subject is inflicted (e.g., has the disease) prior to administration and a prophylactic treatment is one in which the subject is not yet inflicted (does not yet have the disease) prior to administration. In some embodiments, the subject has an increased likelihood of becoming inflicted or is suspected of being inflicted prior to treatment. In some embodiments, the subject is suspected of having an increased likelihood of becoming inflicted. For example, in some cases, the individual has a family history of cancer (e.g., MB tumors).

A "therapeutically effective dose" or "therapeutic dose" is an amount sufficient to effect desired clinical results (i.e., achieve therapeutic efficacy), e.g., reduced tumor size, stabilization of tumor size (e.g., prevention of increased tumor size), reduction or stabilization in the number of cancer cells present in the individual, prevention of metastasis, and the like. A therapeutically effective dose can be administered in one or more administrations. For purposes of this disclosure, a therapeutically effective dose of a CK2 inhibitor (e.g., any CK2 inhibitor above, a CK2-selective inhibitor, e.g., CX-4945, etc.) is an amount that is sufficient to palliate, ameliorate, stabilize, reverse, prevent, slow or delay the progression of the disease state (e.g., MB tumor). Thus, in some cases, a therapeutically effective dose of a CK2 inhibitor (e.g., any CK2 inhibitor above, a CK2-selective inhibitor, e.g., CX-4945, etc.) reduces the size of an MB tumor. In some cases, a therapeutically effective dose of a CK2 inhibitor (e.g., any CK2 inhibitor above, a CK2-selective inhibitor, e.g., CX-4945, etc.) stabilizes the size of an MB tumor (e.g., prevents growth of the tumor). In some cases, a therapeutically effective dose of a CK2 inhibitor (e.g., any CK2 inhibitor above, a CK2-selective inhibitor, e.g., CX-4945, etc.) reduces or stabilized the growth rate of an MB tumor. In some cases, a therapeutically effective dose of a CK2 inhibitor (e.g., any CK2 inhibitor above, a CK2-selective inhibitor, e.g., CX-4945, etc.) increases the life span of the individual being treated. In some cases, a therapeutically effective dose of a CK2 inhibitor (e.g., any CK2 inhibitor above, a CK2-selective inhibitor, e.g., CX-4945, etc.) improves the quality of life for the individual being treated. In some case, treatment using a subject method results in long term regression of the MB tumor (e.g., increases the chance of survival of the individual being treated).

A single therapeutically effective dose or a series of therapeutically effective doses would be able to achieve a desired result in an individual (e.g., reducing or stabilizing MB tumor size). A therapeutically effective dose of a CK2 inhibitor (e.g., any CK2 inhibitor above, a CK2-selective inhibitor, e.g., CX-4945, etc.) can depend on the specific agent used, and in some cases can be 0.5 mg/kg body weight or more (e.g., 1 mg/kg or more, 2 mg/kg or more, 3 mg/kg or more, 4 mg/kg or more, 5 mg/kg or more, 6 mg/kg or more, 7 mg/kg or more, 8 mg/kg or more, 9 mg/kg or more, 10 mg/kg or more, 15 mg/kg or more, 20 mg/kg or more, 25 mg/kg or more, 30 mg/kg or more, 35 mg/kg or more, 40 mg/kg or more, 45 mg/kg or more, 50 mg/kg or more, 55 mg/kg or more, 60 mg/kg or more, 65 mg/kg or more, or 70 mg/kg or more) independently for each agent.

In some cases, a therapeutically effective dose of a CK2 inhibitor (e.g., any CK2 inhibitor above, a CK2-selective inhibitor, e.g., CX-4945, etc.) can be in a range of from 0.5 mg/kg to 100 mg/kg (e.g., from 1 to 100 mg/kg, from 1 to 90 mg/kg, from 1 to 90 mg/kg, from 1 to 85 mg/kg, from 1 to 80 mg/kg, from 1 to 70 mg/kg, from 1 to 60 mg/kg, from 1 to 50 mg/kg, from 1 to 40 mg/kg, from 1 to 30 mg/kg, from 1 to 20 mg/kg, from 1 to 10 mg/kg, from 5 to 100 mg/kg, from 5 to 90 mg/kg, from 5 to 90 mg/kg, from 5 to 85 mg/kg, from 5 to 80 mg/kg, from 5 to 70 mg/kg, from 5 to 60 mg/kg, from 5 to 50 mg/kg, from 5 to 40 mg/kg, from 5 to 30 mg/kg, from 5 to 20 mg/kg, from 5 to 10 mg/kg, from 10 to 100 mg/kg, from 10 to 90 mg/kg, from 10 to 85 mg/kg, from 10 to 80 mg/kg, from 10 to 70 mg/kg, from 10 to 60 mg/kg, from 10 to 50 mg/kg, from 10 to 40 mg/kg, from 10 to 30 mg/kg, from 10 to 20 mg/kg, from 20 to 100 mg/kg, from 20 to 90 mg/kg, from 20 to 85 mg/kg, from 20 to 80 mg/kg, from 20 to 70 mg/kg, from 20 to 60 mg/kg, from 20 to 50 mg/kg, from 20 to 40 mg/kg, from 20 to 30 mg/kg, from 40 to 100 mg/kg, from 40 to 90 mg/kg, from 40 to 85 mg/kg, from 40 to 80 mg/kg, from 40 to 70 mg/kg, from 55 to 100 mg/kg, from 55 to 90 mg/kg, from 55 to 85 mg/kg, from 55 to 80 mg/kg, or from 55 to 70 mg/kg) independently for each agent.

In some cases, a therapeutically effective dose of a CK2 inhibitor (e.g., any CK2 inhibitor above, a CK2-selective inhibitor, e.g., CX-4945, etc.) can be in a range of from 1 mg/kg to 50 mg/kg (e.g., from 1 to 40 mg/kg, from 1 to 30 mg/kg, from 1 to 20 mg/kg, from 5 to 50 mg/kg, from 5 to 40 mg/kg, from 5 to 30 mg/kg, from 5 to 20 mg/kg, from 10 to 50 mg/kg, from 10 to 40 mg/kg, from 10 to 30 mg/kg, from 10 to 20 mg/kg, or from 20 mg/kg to 40 mg/kg) independently for each agent (e.g., for TBB, for CX-4945). In some cases, a therapeutically effective dose of a CK2 inhibitor (e.g., any CK2 inhibitor above, a CK2-selective inhibitor, e.g., CX-4945, etc.) can be in a range of from 10 mg/kg to 40 mg/kg (e.g., from 10 to 35 mg/kg, or from 10 to 30 mg/kg, or from 20 mg/kg to 40 mg/kg) independently for each agent (e.g., for TBB, for CX-4945).

In some cases, a therapeutically effective dose of a CK2 inhibitor (e.g., any CK2 inhibitor above, a CK2-selective inhibitor, e.g., CX-4945, etc.) can be in a range of from 25 mg/kg to 100 mg/kg (e.g., from 25 to 100 mg/kg, from 40 to 100 mg/kg, from 50 to 100 mg/kg, from 60 to 100 mg/kg, from 25 to 90 mg/kg, from 40 to 90 mg/kg, from 50 to 90 mg/kg, or from 60 to 90 mg/kg) independently for each agent (e.g., for TBB, for CX-4945). In some cases, a therapeutically effective dose of a CK2 inhibitor (e.g., any CK2 inhibitor above, a CK2-selective inhibitor, e.g., CX-4945, etc.) can be in a range of from 60 mg/kg to 90 mg/kg (e.g., from 65 to 85 mg/kg, or from 70 to 80 mg/kg) independently for each agent (e.g., for TBB, for CX-4945).

The dose required to achieve a desired result can be proportional to the amount of time between doses and inversely proportional to the number of doses administered. Thus, as the frequency of dosing increases, the required dose decreases. The optimization of dosing strategies will be readily understood and practiced by one of ordinary skill in the art.

Dosage and frequency may vary depending on the half-life of the agent (e.g., CK2 inhibitor) in the patient. It will be understood by one of skill in the art that such guidelines will be adjusted for the molecular weight of the active agent. The dosage may also be varied for localized administration, e.g. intracranial, or for systemic administration, e.g. i.m., i.p., i.v., and the like.

Co-Administration

Two or more of the above described CK2 inhibitors (e.g., CK2-selective inhibitors) can be co-administered, and administration of a CK2 inhibitor (e.g., a CK2-selective inhibitor such as CX-4945) could be readily combined with other therapies for cancer (e.g., medulloblastoma). As such, in some cases, a subject composition (that includes a CK2 inhibitor, e.g., a CK2-selective inhibitor such as CX-4945) is co-administered with another agent, e.g., a second CK2 inhibitor (e.g., CK2-selective inhibitor), or co-administered with another therapy for cancer (e.g., medulloblastoma). The terms "co-administration", "co-administer", and "in combination with" include the administration of two or more therapeutic agents (e.g., two or more CK2 inhibitors) either simultaneously, concurrently or sequentially within no specific time limits. In one embodiment, the agents are present in the cell or in the subject's body (in their blood stream) at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject composition (that includes a CK2 inhibitor, e.g., a CK2-selective inhibitor such as CX-4945) (e.g., formulated as a pharmaceutical composition) is co-administered with a cancer therapeutic drug (e.g., a therapeutic drug to treat medulloblastoma). Such administration may involve concurrent (i.e. at the same time), prior, or subsequent administration of the agent/drug/antibody with respect to the administration of an agent or agents of the disclosure. A person of ordinary skill in the art would have no difficulty determining the appropriate timing, sequence and dosages of administration for particular drugs and compositions of the present disclosure.

In some cases, a subject composition (that includes a CK2 inhibitor, e.g., a CK2-selective inhibitor such as CX-4945) (e.g., formulated as a pharmaceutical composition) is co-administered with a hedgehog pathway inhibitor (e.g., a SMO inhibitor, GDC-0449, and the like). In some cases, a subject composition (that includes a CK2 inhibitor, e.g., a CK2-selective inhibitor such as CX-4945) (e.g., formulated as a pharmaceutical composition) is co-administered with a chemotherapeutic agent (e.g., a nucleoside analog/antimetabolite, a plant alkaloid/alkylating/alkylating-like agent). In some cases, a subject composition (that includes a CK2 inhibitor, e.g., a CK2-selective inhibitor such as CX-4945) (e.g., formulated as a pharmaceutical composition) is co-administered with an EGFR inhibitor. Additional examples of compounds with which a subject composition (that includes a CK2 inhibitor, e.g., a CK2-selective inhibitor such as CX-4945) (e.g., formulated as a pharmaceutical composition) can be co-administered include but are not limited to: cisplatin, vincristine/vinblastine, cyclophosphamide, cyclophosphamide plus a hedgehog inhibitor, and gemcitabine/pemetrexed.

A subject composition (that includes a CK2 inhibitor, e.g., a CK2-selective inhibitor such as CX-4945) need not be, but is optionally formulated with one or more agents that potentiate activity, or that otherwise increase the therapeutic effect. These can be used in the same dosages and with administration routes as used herein or from 1 to 99% of the employed dosages. In some embodiments, treatment is accomplished by administering a combination (co-administration) of a subject CK2 inhibitor, e.g., a CK2-selective inhibitor such as CX-4945, and an agent that treats cancer (e.g., medulloblastoma). Thus, also envisioned herein are compositions and kits (and methods that use the compositions and/or kits) that include: (a) a CK2 inhibitor, e.g., a CK2-selective inhibitor such as CX-4945; and (b) an agent used for treatment of medulloblastoma.

Delivery/Administration

A CK2 inhibitor (e.g., a CK2-selective inhibitor such as CX-4945) can be administered by any suitable means (e.g., systemic or local), including topical, oral, parenteral, intravenous, intracranial, intratumoral, intrapulmonary, and intranasal. Parenteral infusions include intramuscular, intravenous (bollus or slow drip), intraarterial, intraperitoneal, intrathecal or subcutaneous administration. A CK2 inhibitor (e.g., a CK2-selective inhibitor such as CX-4945) can be administered in any manner which is medically acceptable. This may include by injection (e.g., by parenteral routes such as intravenous, intravascular, intraarterial, subcutaneous, intramuscular, intratumoral, intraperitoneal, intraventricular, intracranial, or intraepidural), or others as well as oral, nasal, ophthalmic, rectal, or topical. Sustained release administration is also specifically included in the disclosure, by such means as depot injections or erodible implants. For example, in some cases TBB is administered by intraperitoneal injection (IP). In some cases CX-4945 is administered orally. In some cases CX-4945 is administered intrathecally (within the CSF), e.g., for patients with metastatic disease. Some agents can also applied directly to the area after the tumor is resected, e.g., by local injection, or by placing drug infused patties.

As noted above, a CK2 inhibitor (e.g., a CK2-selective inhibitor such as CX-4945) can be formulated with a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. In some cases, an effective amount is an amount that reduces tumor size (e.g., MB tumor size) in the individual. An effective amount can be determined on an individual basis and can be based, in part, on consideration of the symptoms to be treated and results sought. An effective amount can be determined by one of ordinary skill in the art employing such factors and using no more than routine experimentation.

A CK2 inhibitor (e.g., a CK2-selective inhibitor such as CX-4945) can be administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear a CK2 inhibitor (e.g., a CK2-selective inhibitor such as CX-4945) by non-covalent associations, such as non-covalent bonding or by encapsulation. The nature of the carrier can be either soluble or insoluble for purposes of the disclosure. Those skilled in the art will know of other suitable carriers for binding a CK2 inhibitor (e.g., a CK2-selective inhibitor such as CX-4945), or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of a CK2 inhibitor (e.g., a CK2-selective inhibitor such as CX-4945) can be determined by standard pharmaceutical procedures in cell cultures and/or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

Measuring an Expression Level

In some cases, a subject method of treatment (one that includes administration of a CK2 inhibitor, e.g., a CK2-selective inhibitor such as CX-4945) includes a step of measuring an expression level of Gli1 RNA and/or CSNK2A1 RNA in a sample (e.g., a biological sample such as a biopsy sample and/or blood sample) from an individual (e.g., one who is being treated). An expression level of an RNA can be measured using any convenient method (e.g., quantitative RT-PCR, microarray, RNA sequencing such as high throughput sequencing, etc.). As Gli1 is a transcriptional target of the HH pathway, the expression level of Gli1 RNA can be used as an indicator of whether a subject treatment method is having the expected result at the molecular level. For example, in some cases, administration of a subject composition (e.g., a composition that includes a CK2 inhibitor, e.g., a CK2-selective inhibitor such as CX-4945) should cause a decrease in the expression level of Gli1 RNA. As such, in some cases, an expression level of Gli1 RNA can be measured after treatment to monitor the progress of treatment (e.g., where a decrease in Gli1 RNA after/during treatment indicates that the composition is having the desired effect at the molecular level). As such, in some cases, an expression level of Gli1 RNA is measured prior to treatment in order to establish a baseline expression level (e.g., in order to compare later measured levels after treatment has begun).

In some cases, an expression level of CSNK2A1 RNA is measured in a sample (e.g., a biological sample such as a biopsy sample and/or blood sample) from an individual in order to predict whether the individual has a poor prognosis. For example, as described in the working examples below, the inventors have discovered that MB patients with low levels of CSNK2A1 RNA expression have a much better chance of survival compared to MB patients with high levels of CSNK2A1 RNA. As such, like Gli1 RNA expression levels, in some cases expression levels of CSNK2A1 RNA can be used to monitor treatment. In other words, the expression level of CSNK2A1 RNA can be used as an indicator of whether a subject treatment method is having an effect. For example, in some cases, administration of a subject composition (e.g., a composition that includes a CK2 inhibitor, e.g., a CK2-selective inhibitor such as CX-4945) should cause a decrease in the expression level of CSNK2A1 RNA. As such, in some cases, an expression level of CSNK2A1 RNA can be measured after treatment to monitor the progress of treatment (e.g., where a decrease in CSNK2A1 RNA after/during treatment indicates that the composition is having the desired effect). As such, in some cases, an expression level of CSNK2A1 RNA is measured prior to treatment in order to establish a baseline expression level (e.g., in order to compare later measured levels after treatment has begun). In some cases, an expression level of CSNK2A1 RNA is measured to help determine whether a given individual is high risk (e.g., has a decreased chance of survival), where an increased expression level of CSNK2A1 RNA (e.g., relative to a reference such as a predetermined threshold level and/or a CSNK2A1 RNA expression level measured from one or more patients without MB or with low risk MB) would indicate higher risk. Such an analysis could be used, for example, to determine whether a patient should be treated with a subject method. For example, in some cases high CSNK2A1 RNA expression levels (e.g., relative to a reference such as a predetermined threshold level and/or a CSNK2A1 RNA expression level measured from one or more patients without MB or with low risk MB) would indicate that the patient should be treated (or perhaps treated more aggressively, e.g., by co-administration with another therapy/drug).

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-19 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below. In all of the aspects listed below, it is also envisioned that 'method of treating' aspects can be re-written as 'composition for use' aspects (e.g., composition for use in the methods listed below).

1. A method of treating an individual who has a medulloblastoma tumor, the method comprising: administering a composition comprising a casein kinase II (CK2) inhibitor to the individual at a dose sufficient to reduce the size and/or growth rate of the medulloblastoma tumor.

2. The method according to 1, wherein the medulloblastoma tumor is a hedgehog-dependent medulloblastoma tumor.

3. The method according to 1, wherein the medulloblastoma tumor is a hedgehog-independent medulloblastoma tumor.

4. The method according to 1, wherein the medulloblastoma tumor is smoothened inhibitor-resistant (SMO inhibitor-resistant).

5. The method according to any one of 1-4, wherein the composition comprises a CK2-selective inhibitor.

6. The method of 5, wherein the composition comprises a CK2-selective inhibitor selected from: 5-(3-Chloroanilino) benzo[c][2,6]naphthyridine-8-carboxylic acid (CX-4945), 1,2,5,8-tetrahydroxyanthraquinone (quinalizarin), 4,5,6,7-tetrabromo-2H-benzotriazole (TBB), and 1-hydroxy-6-methyl-2-propylsulfonylthieno[3,2-d]diazaborinine (TDB).

7. The method according to 6, wherein the composition comprises 4,5,6,7-tetrabromo-2H-benzotriazole (TBB).

8. The method according to any one of 1-6, wherein the medulloblastoma is resistant to 4,5,6,7-tetrabromo-2H-benzotriazole (TBB).

9. The method according to any one of 1-8, wherein the composition comprises 5-(3-Chloroanilino)benzo[c][2,6] naphthyridine-8-carboxylic acid (CX-4945).

10. The method according to any one of 1-9, wherein the composition comprises 1,2,5,8-tetrahydroxyanthraquinone (quinalizarin).

11. The method according to any one of 1-10, wherein the composition comprises 1-hydroxy-6-methyl-2-propylsulfonylthieno[3,2-d]diazaborinine (TDB).

12. The method according to any one of 1-11, wherein said administering comprises local administration.

13. The method according to any one of 1-12, wherein said administering comprises systemic administration.

14. The method according to 13, wherein said systemic administration comprises oral administration.

15. The method according to any one of 1-14, further comprising a step of measuring an expression level of Gli1 RNA in a biological sample from the individual.

16. The method according to any one of 1-15, further comprising a step of measuring an expression level of CSNK2A1 RNA in a biological sample from the individual.

17. The method according to 15 or 16, wherein the biological sample is a biopsy from the medulloblastoma tumor.

18. The method according to any one of 1-17, wherein the dose is sufficient to cause long term regression of the medulloblastoma tumor.

19. The method according to any one of 1-18, wherein the dose is sufficient to increase the chance of survival of the individual.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1: Developmental Phosphoproteomic Approach Identifies Casein Kinase 2 (CK2) as a Therapeutic Target for Treating Medulloblastoma The inventors realized that because kinases activate multiple important substrates, they are therapeutic targets that have the potential to be more resistant to tumor evolution and effective in a broad range of tumor subtypes. In the experiments presented herein, a "developmental phosphoproteomic" approach was implemented in granule neuron precursors (GNPs); the developmental cell of origin of the pediatric brain tumor medulloblastoma. Through deep quantitative phosphoproteomic evaluation (in the experiments presented below), an unprecedented view was provided of the post-translational regulation of this single transit amplifying population at its moment of differentiation in vivo, and the dynamic regulation of thousands of phosphorylation events were characterized during the proliferative period of GNP development. As described below, casein kinase 2 (CK2) was identified as a putative kinase driving hundreds of phosphorylation events occurring during peak proliferation, many involving substrates of known importance for tumor growth and survival. CK2 was demonstrated (see below) to be required for cerebellar growth and to affect Hh signaling downstream of Smoothened (SMO), at the level of Gli2 stability and Gli2 targeting of H3K27ac marked genes.

Accordingly, CK2 blockade inhibited intracranial growth and resulted in long-term regression of both SMO inhibitor-sensitive and resistant MB.

Results

In the developing mouse cerebellum, granule neuron precursor (GNP) proliferation occurs during the first few weeks of postnatal life (FIG. 1a). This period of transit amplification begins at P1 when Atoh-1 positive GNPs begin their first round of division in the external granule layer (EGL), driven by the hedgehog signaling pathway (Shh, FIG. 3a). By P7 Atoh-1 positive GNPs are at peak proliferation in the outer EGL (oEGL) and post-mitotic Tag-1 positive GNPs in the inner EGL (iEGL) where they extend two lateral processes prior to migrating into the inner granule layer (IGL) and undergoing terminal differentiation. By P14, the majority of GNPs have migrated into the IGL and the remaining Atoh-1 positive GNPs have undergone their final division.

Figure 1D:
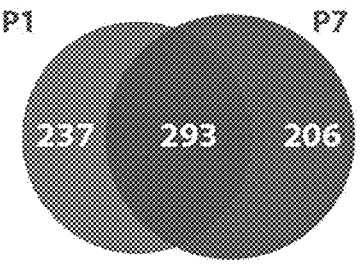
Figure 1D:
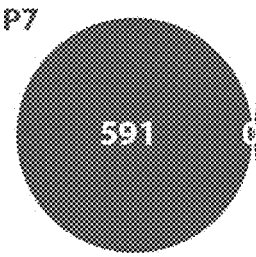

To characterize this period of transit amplification and early differentiation, Tandem Mass Tags (TMT)-based quantitative proteomics and phosphoproteomics were used to evaluate relative protein levels and protein phosphorylation events in Atoh-1 positive GNPs purified at P1, P7 and P14 as well as in medulloblastoma (MB) samples generated from Ptch1+/− mice (FIG. 1b). GNPs were purified via percoll fractionation, which resulted in 96.2% purity of atoh-1 positive cells and <1% tag-1 positive cells (sup 1a). Proteomic evaluation identified 111,823 unique peptides from 8,027 proteins, of which 7,825 were quantified (1% FDR). All time points demonstrate strong correlations between biological replicates ($R^2$=0.81, sup1a). 4.1% of proteins changed >1.5-fold between P1 and P7, and 25.4% changed >1.5-fold between P7 and P14 (FIG. 1d). Markers of proliferating GNPs and hedgehog signaling were highest in P1 and P7 (cyclins/CDKs, Atoh1, Gli2, SUFU). In contrast, known factors involved in neural differentiation had an unexpected biphasic expression pattern with some rising in P7 (Neurod1/2, NHLH1) and others rising at P14 (BMP2k, Vsnl1).

Consensus hierarchical clustering demonstrated a distinct state change between proliferating (P1 and P7) and early post-mitotic (P14) GNPs, with P7 sharing 59% of its highest and lowest expressed proteins (>2 SD) with P1 and 0% with P14 (Fig. d). Similarly, GO-term enrichment of the top changing proteins in P7 demonstrated a 90% overlap in enriched terms with P1 GNPs but only 1% overlap P14 GNPs (FIG. 1d), suggesting that the approach used had a dynamic range capable of identifying both subtle state changes (P1 vs P7) and dramatic switches in cell identify (P7 vs P14).

While P1 and P7 GNPs were both strongly enriched for terms associated with cell cycle regulation, proliferation and growth (1e/f), they also demonstrated unexpected differences in underlying biological processes. For example, early GNPs (P1) were enriched for terms associated with biosynthesis (fatty acid and macromolecule biosynthesis) and metabolism (protein, macromolecule, cofactor, glucose metabolism) while P7 GNPs were enrichment for terms associated with neural development (neurogenesis, CNS development) consistent with the first peak in expression of proteins associated with GNP differentiation. While often considered synonymous proliferating cell populations, this may reflect the differences between transit amplifying cells that are initiating a period of sustained proliferation (P1) versus at peak proliferation and positioning themselves towards differentiation (P7). P7 GNPs also had higher expression of proteins involved in cellular responses to stress and DNA damage and P14 GNPs had the lowest expression of telomere-associated proteins. This may be indicative of the damage to the genome that invariably accrues during periods of massive expansion and is wholly consistent with previous studies showing 30% of GNPs undergo apoptosis.

Unlike the proliferative time points, P14 GNPs were enriched for terms associated with neural differentiation (cell polarity, cell migration, axonogenesis, neuron differentiation) as well as unexpected terms including several cell signaling pathways (EGF signaling, JNK/JAK/Rho signaling) (FIG. 1d). They also displayed an increase in many proteins related to ion homeostasis consistent with their pending transition to terminally differentiated, excitable granule neurons. This is particularly notable in light of evidence that abnormal cell membrane homeostasis is a hallmark of MB and increased membrane excitability is incompatible with MB proliferation.

Figure 2A:
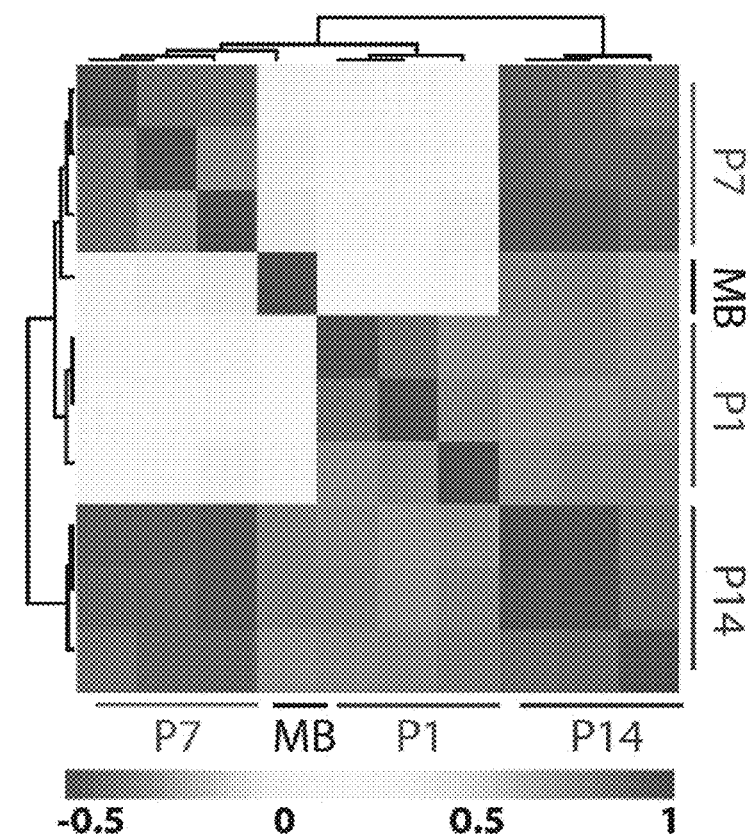
FIG. 2a-2g. Phosphorylation motif analysis in GNPs.
Figure 2A:
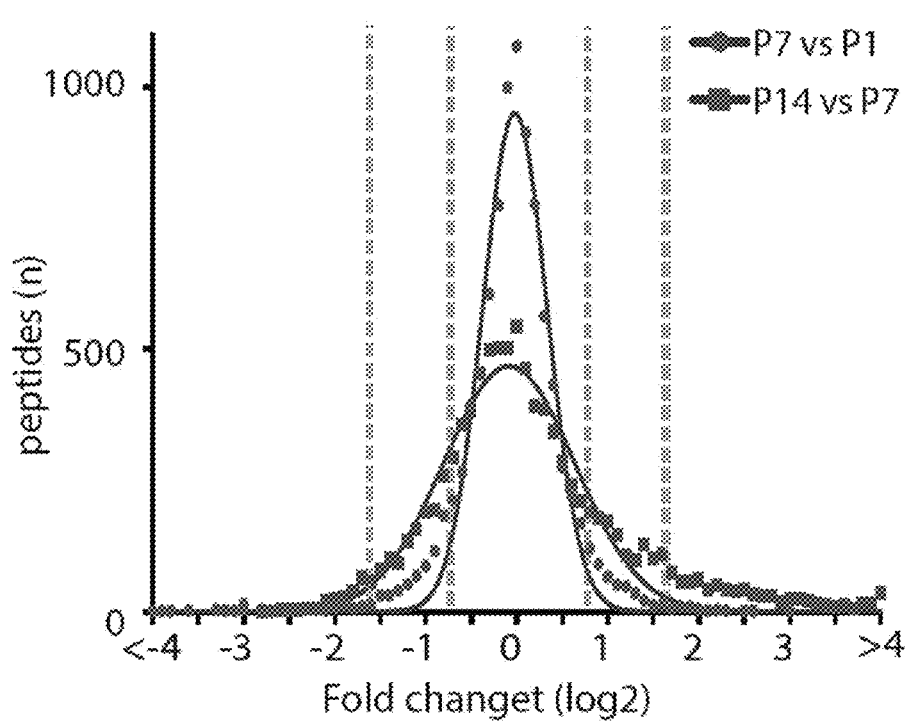
Figure 2B:
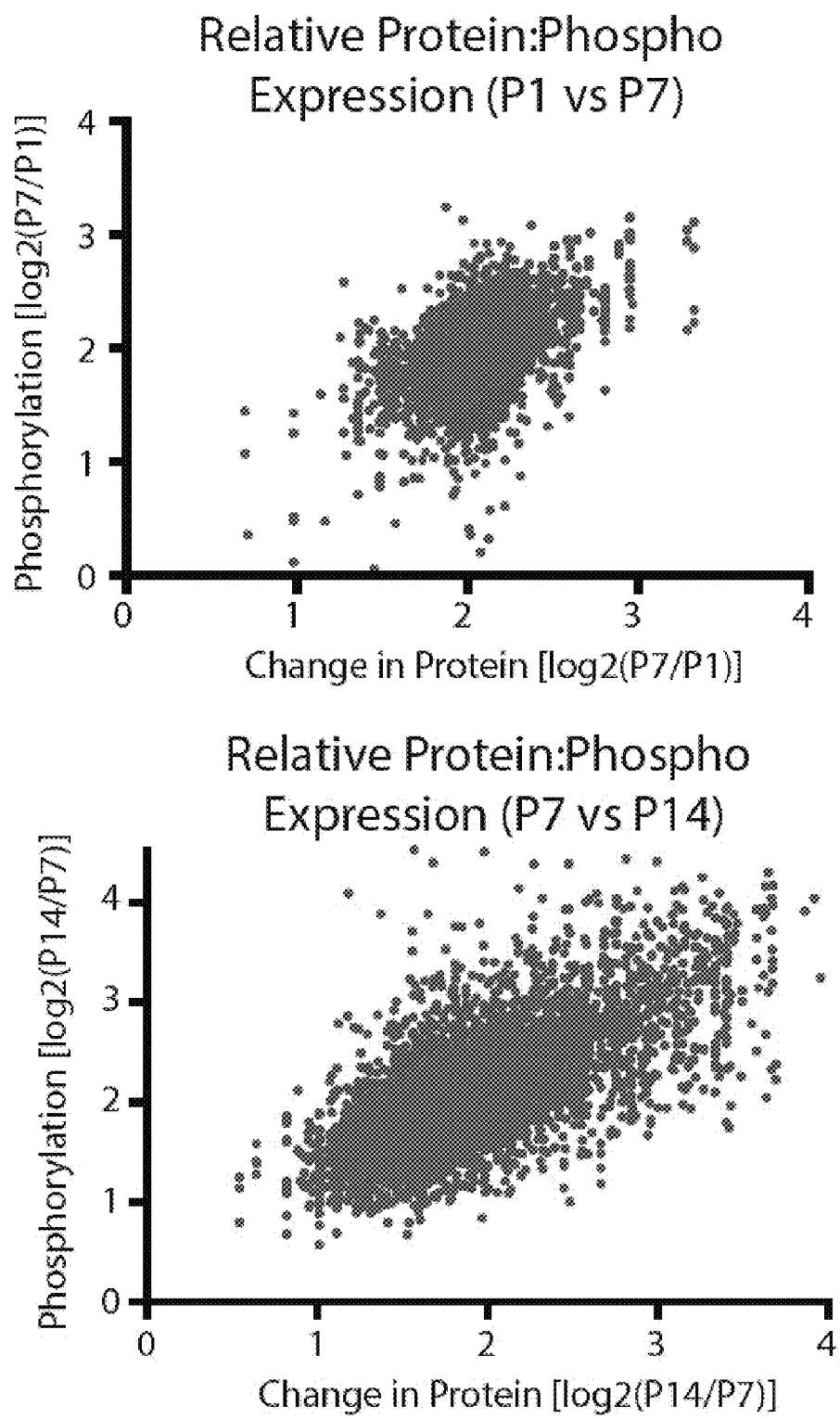

To investigate the role of post-translation modification in this period of development, a different phosphoproteomic dataset was used. Phosphoproteomic evaluation identified 12,615 unique phosphopeptides of which 9,311 were quantified (FDR<1%). 39% of proteins had a single phosphorylation event while 22% had 2, 38% had 3 or more. 88% of events captured occurred on serine while 11% occurred on threonine or tyrosine. When normalized to protein levels, there was a 2-fold change in 5.0% of all phosphorylation events between P1 and P7 and 21.4% of phosphorylation events between P7 and P14 (FIG. 1d). Several phosphorylation events occurred in known Hh pathway components (Gli1/2/3, Sufu), as well as established cell cycle regulators (Rb1), drivers of neural differentiation (Bmp2k, NeuroD2), and GNP lineage markers (Atoh1) (FIG. 2a). As with protein expression, phosphorylation patterns were largely as expected with activation of hedgehog and cell cycle regulators in P1 and P7 and differentiation proteins in P7 and P14.

Figure 1E:
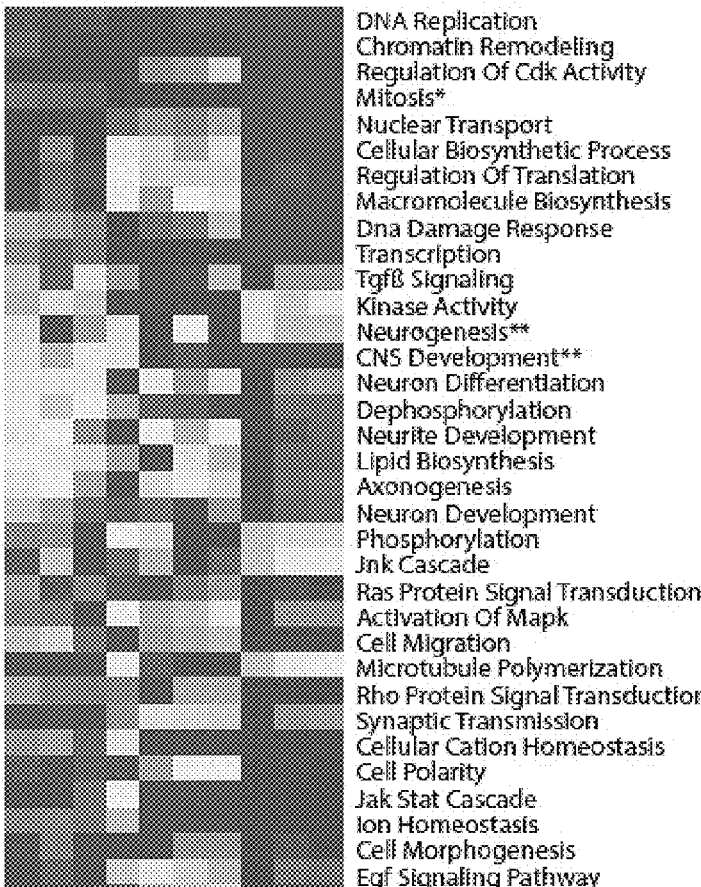
Figure 1F:
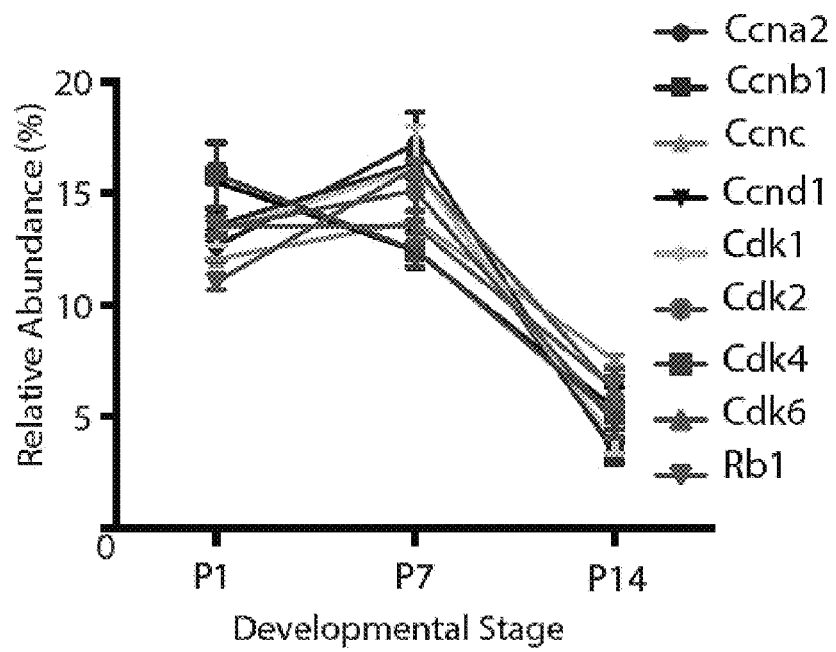
Figure 1F:
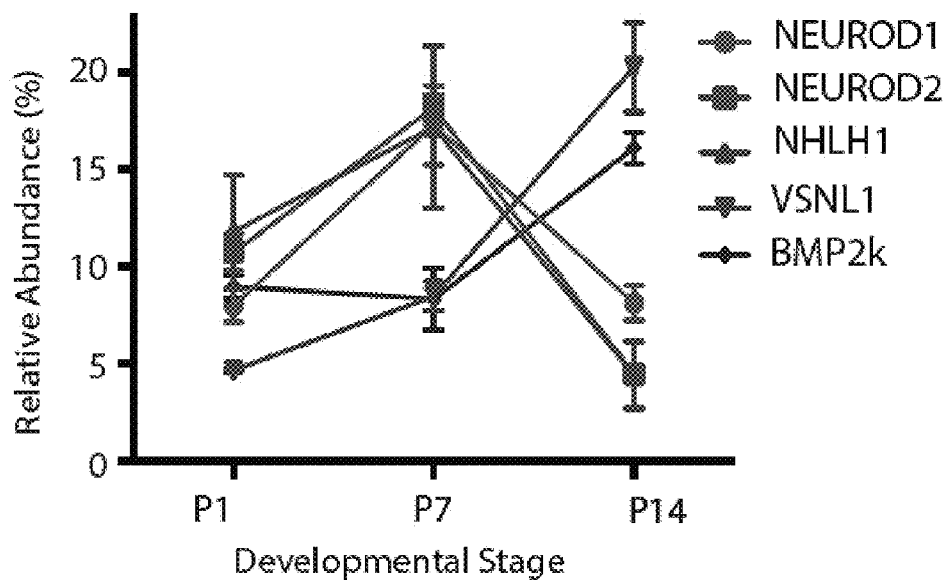
Figure 2C:
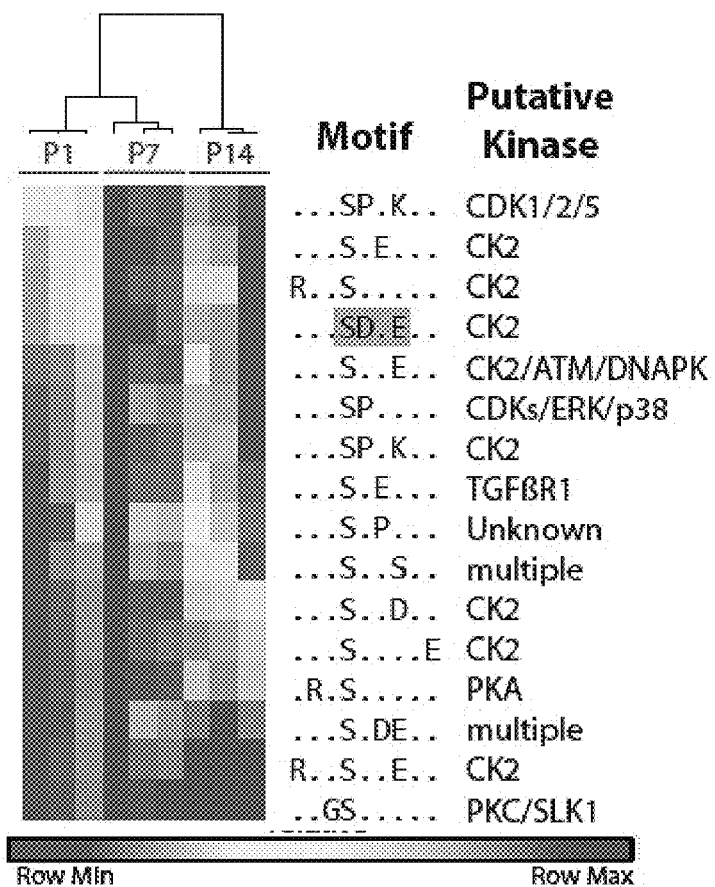
Figure 2C:
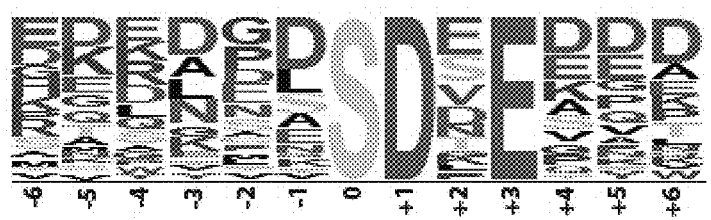
Figure 2D:
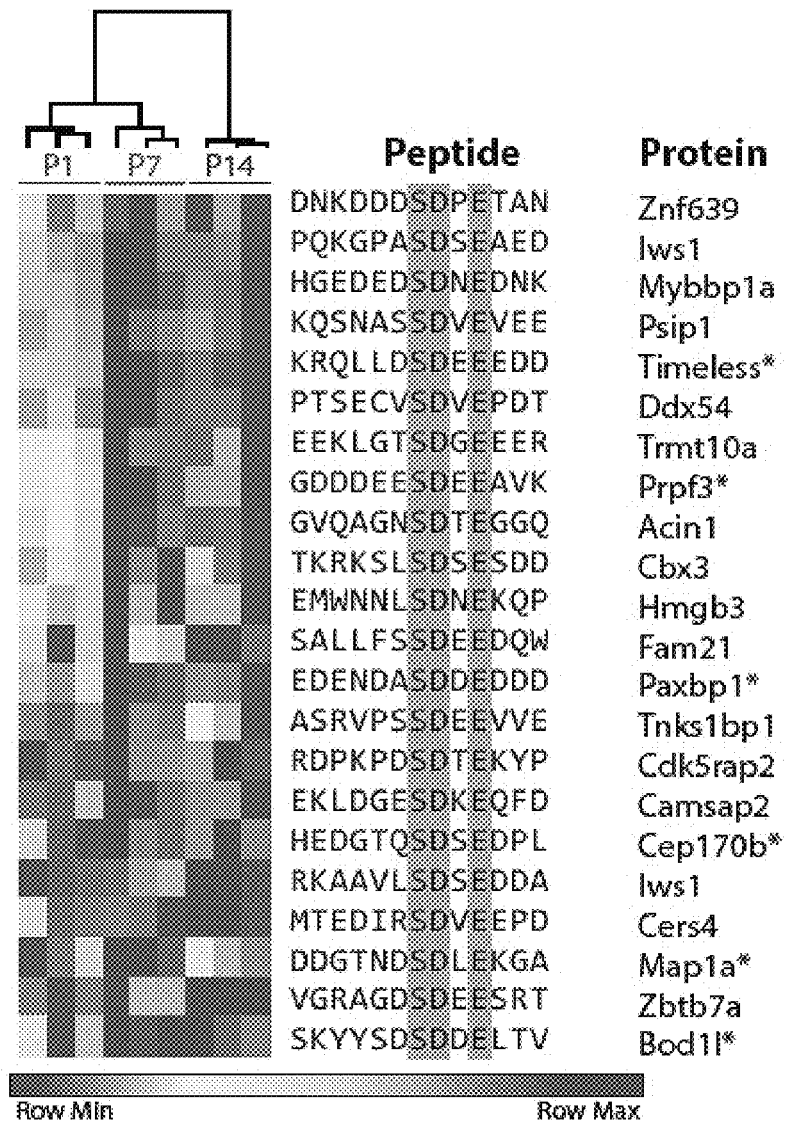

To determine whether specific kinases were responsible for bulk phosphorylation events observed in the dataset, motif analysis was performed revealing statistically significant enrichment of 16 phosphomotifs, some of which were expected (CDK, pKA, SLK1) but half of which unexpectedly correlated with putative CK2 motifs which are characterized by acidic residues (Aspartate and/or Glutamate) downstream of a phosphorylated Serine (or Threonine) (FIG. 2c-2d). Remarkably, >50% of all changing phosphorylation sites observed in the study harbored a putative CK2 motif (p<0.00001), including known CK2 substrates (Maple, Cep170b, Paxbp1, Timeless) and previously uncharacterized CK2 substrates and/or phosphosites (FIG. 2d). In keeping with the findings on GO-TERM enrichment that P7 GNPs are enriched for kinase activity and phosphorylation (FIG. 1e), most putative CK2-mediated phosphorylation events were highest in P7 GNPs.

Figure 2E:
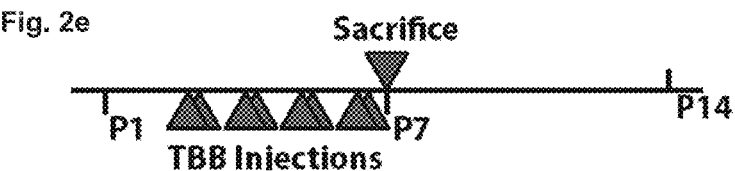
Figure 2F:
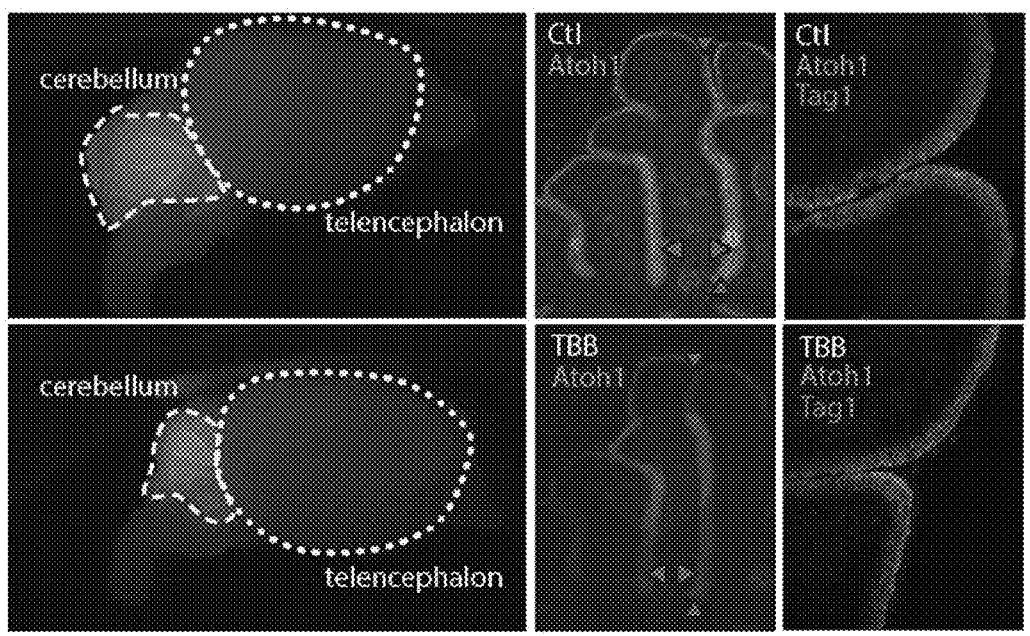
Figure 2G:
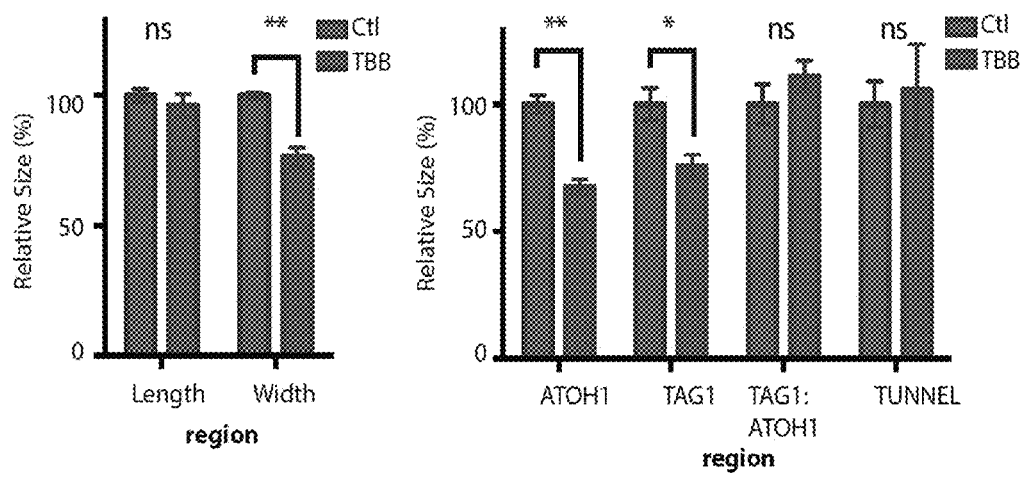

The role of CK2 in cerebellar development was next investigated by injecting mice with the CK2 inhibitor TBB between P3-P7 (FIG. 2e). CK2 inhibition resulted in a decrease in cerebellar size, GNP-dependent foliary width and number of ATOH-1 positive proliferating GNPs (FIG. 2e-2f). In contrast, there was no significant change in foliary length, rate of differentiation or apoptosis, suggesting that the major effect of CK2 inhibition was on GNP proliferation.

Figure 3A:
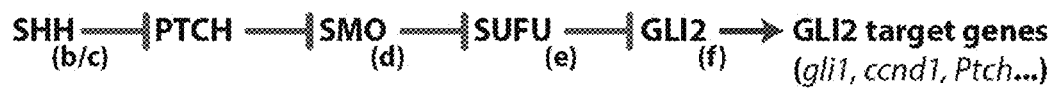
FIG. 3a-3g. CK2 is required for Hh signaling through regulation of Brd4-dependent Gli transcription.

Given that GNP proliferation is driven by hedgehog signaling (Hh), it was next determined whether CK2 is necessary for Hh pathway activation. In canonical Hh signaling, Hh ligands (Shh, Ihh, Dhh) bind the multi-pass cell surface receptor Patched (Ptch1) which results in de-repression of the G protein-coupled receptor Smo and activation of the otherwise latent Gli2 zinc-finger transcription factor via suppression of suppressor of fused (SUFU) (FIG. 3a). Gli2 subsequently drives proliferation through transactivation of promoters of Hh target genes, including cell cycle regulators Ccnd1 and Mycn as well as hedgehog pathway components Gli1 and Ptch.

Figure 3B:
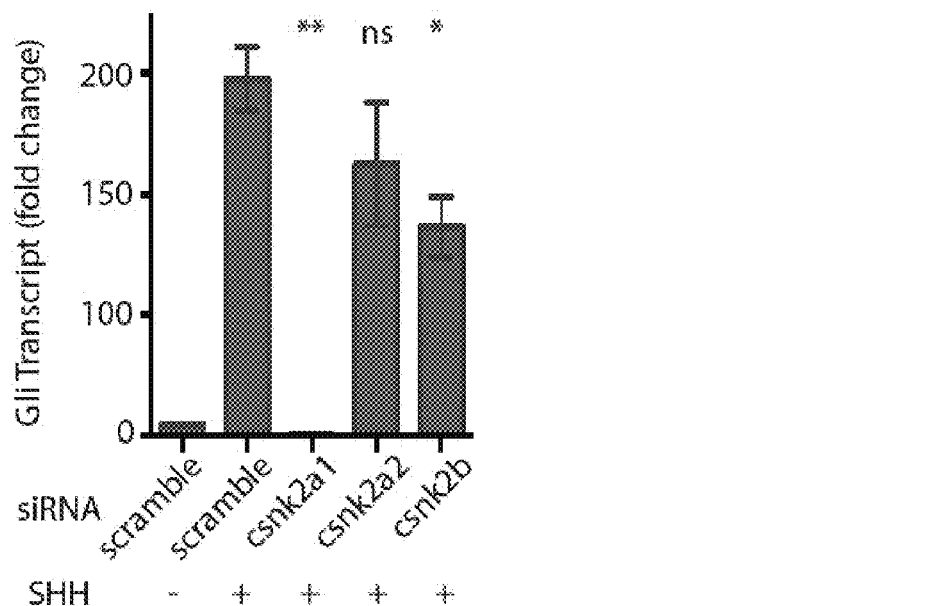
Figure 3C:
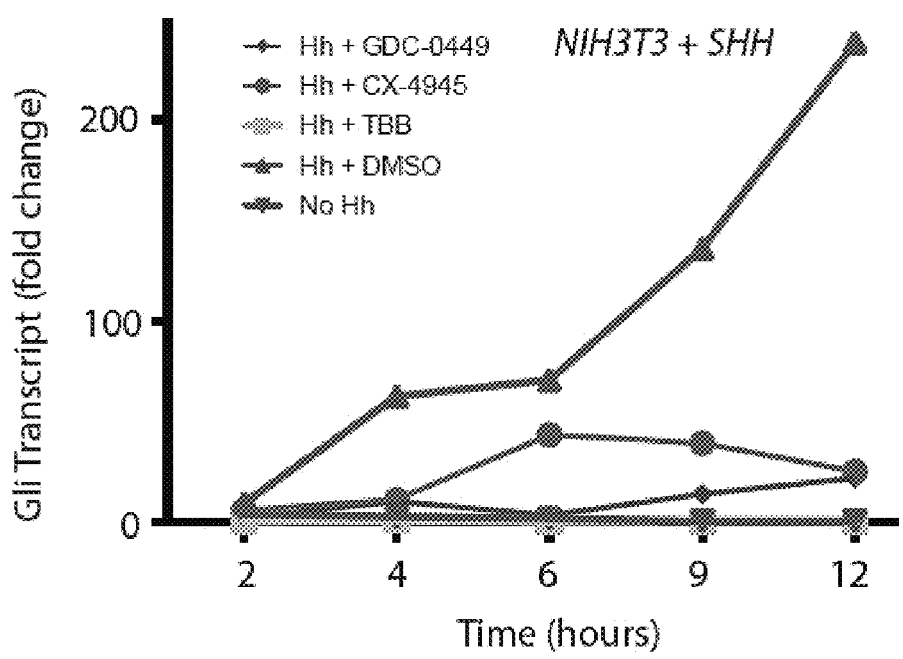

SHH ligand-induced activation of NIH 3T3 cells resulted in an increase in Gli1 mRNA levels, which was inhibited by pooled shRNA-mediated knockdown of Csnk2a1, and to a lesser extent Csnk2a2 and Csnk2b (FIG. 3b) as well as two structurally distinct but highly specific CK2 inhibitors TBB and CX-4945 (FIG. 3c), as early as 4 h post exposure. Taken together, these results demonstrate that CK2 is necessary for ligand-induced Hh transcriptional activation.

Figure 3D:
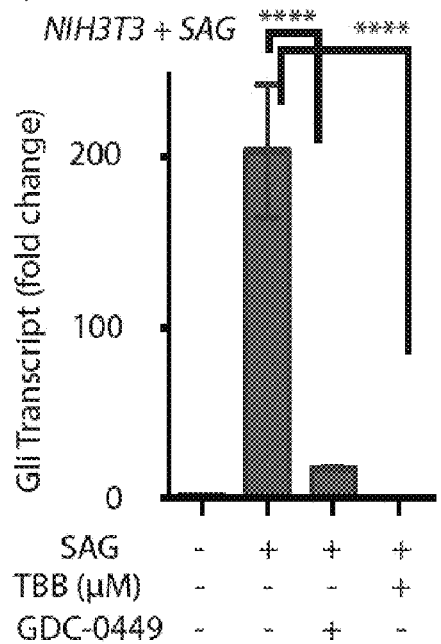
Figure 3E:
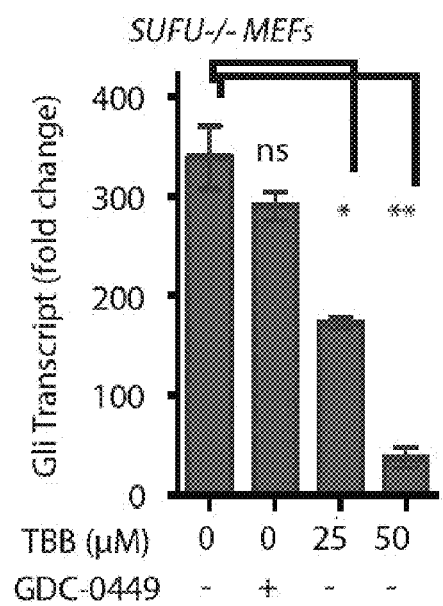
Figure 3F:
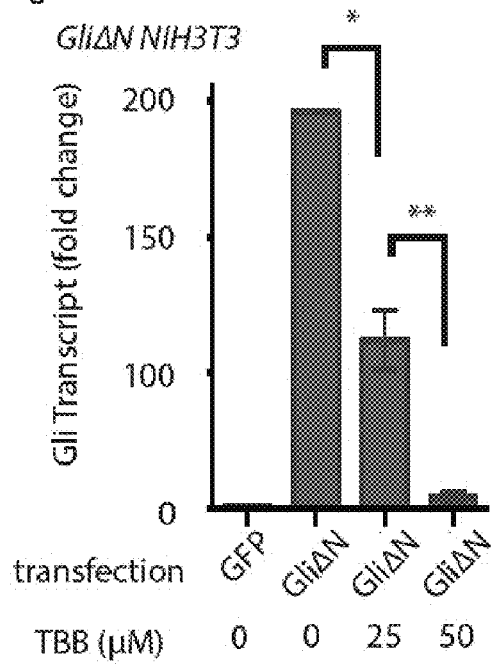
Figure 3G:
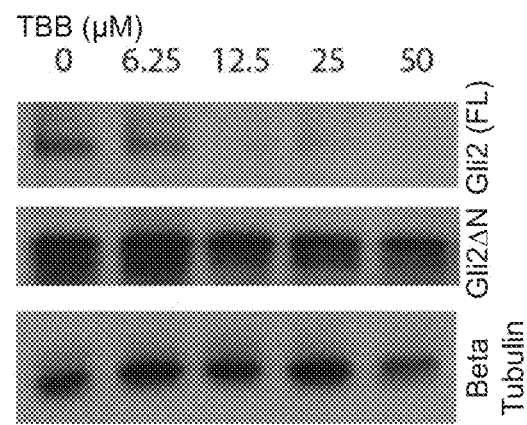

Epistasis studies were next performed to determine where in the hedgehog pathway CK2 acts. The effect of TBB was examined: (i) in NIH 3T3s stimulated with SAG, a SMO agonist, (ii) in Sufu−/− mouse embryonic fibroblasts (MEF), and (iii) in NIH 3T3 cells overexpressing GLI2 (FIG. 3d-3f). Increased Gli1 mRNA levels were observed in SAG treated groups and in Sufu−/− MEFs, which was substantially decreased by TBB in a dose-responsive manner (FIG. 3d-3e). In stark contrast to TBB treatment, SUFU−/− MEFs had no significant change in Gli transcript levels after treatment with the Smo inhibitor GDC-0449 (FIG. 3e). Forced expression of the truncated, active and constitutively nuclear form of murine Gli2 (HA-Gli2ΔN) in 3T3 cells resulted in increased Gli1 mRNA levels, which was inhibited by TBB (FIG. 3f). Notably, no decrease in GLI2 protein driven off the CMV promoter-expression vector after TBB treatment was observed, in contrast to a decreases in endogenous, full length Gli2 mRNA levels (FIG. 3g). This suggests CK2 inhibition affects endogenous full-length Gli2 stability, but TBB's affect on Gli target gene transcription in Gli2ΔN cells is not due to regulation of the plasmid promoter nor the stability of expressed Gli2ΔN protein, but rather on the interaction of Gli2 on the endogenous Gli2 target gene promoters.

Previous studies showed that Hh signaling requires Brd4, a bromodomain and extra C-terminal (BET) protein, for Gli target gene transcription. It was therefore investigated whether CK2 regulates Brd4-mediated transactivation of the Gli promoters. Chromatin immunoprecipitation (ChIP) was performed in NIH3T3s stimulated with SHH using anti-Brd4 antibodies, followed by quantitative PCR (qPCR) of regions flanking the transcription start sites within the Gli1 and Gli2 promoters.

Brd4 occupancy at both Gli1 and Gli2 promoters was blocked by the addition of TBB (FIG. 3e). Given that Brd4's primary role as a reader of H3K27ac histone modifications, whether the effect of TBB on Gli target genes correlated with H3K27ac in GNP on a genome-wide scale was next examined. GNPs were purified from P7 mice following two injections of TBB over an 18 h period. Chipseq using H3K27ac and Gli2 antibodies were performed and Gli target genes were binned into either 'high' or low H3K27ac' groups. In keeping with effect of TBB on Brd4 occupancy, 'high' H3K27ac marked Gli target genes demonstrated a statistically significant decrease in Gli binding when compared to low H3K27ac marked genes, suggesting TBB was inhibiting Gli2 binding in an H3K27ac dependent manner. Interestingly, different Gli target genes demonstrated different H3K27ac patterns in NIH3T3's and GNPs. For example, Gli1 had low H3K27ac in GNPs but high H3K27ac in NIH 3T3's. In contrast, Gli2 and Ptch both had high H3K27ac marks in both GNPs and NIH 3T3's. These differences were mirrored by the effect of TBB on transcript levels following Hh stimulation, where TBB resulted in no change in Gli1 levels in GNPs but a dramatic decrease in Gli1 levels in NIH 3T3's. Similarly, TBB was effective at decreasing both Ptch and Gli2 levels in both GNPs and 3T3's.

Figure 4A:
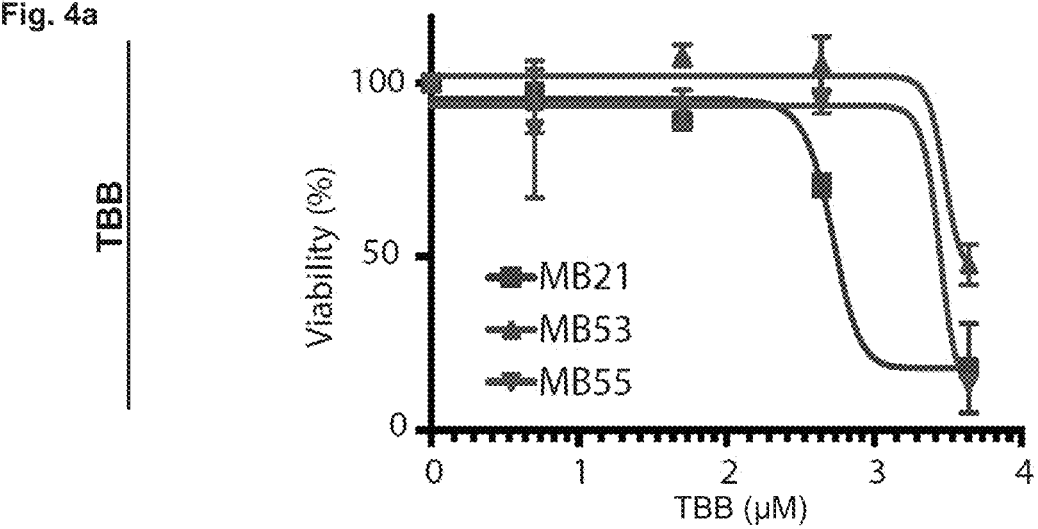
FIG. 4a-4g. Efficacy of CK2 inhibitors on MB growth, in vivo.
Figure 4A:
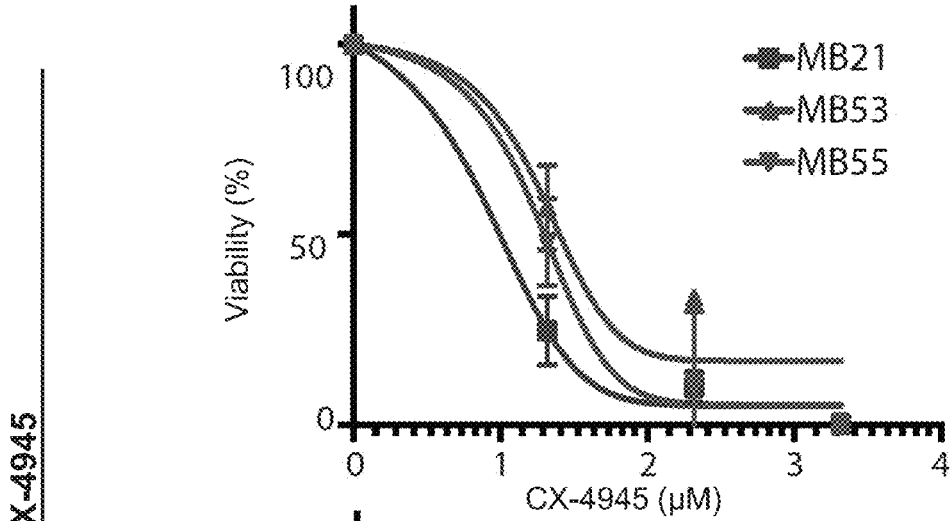
Figure 4A:
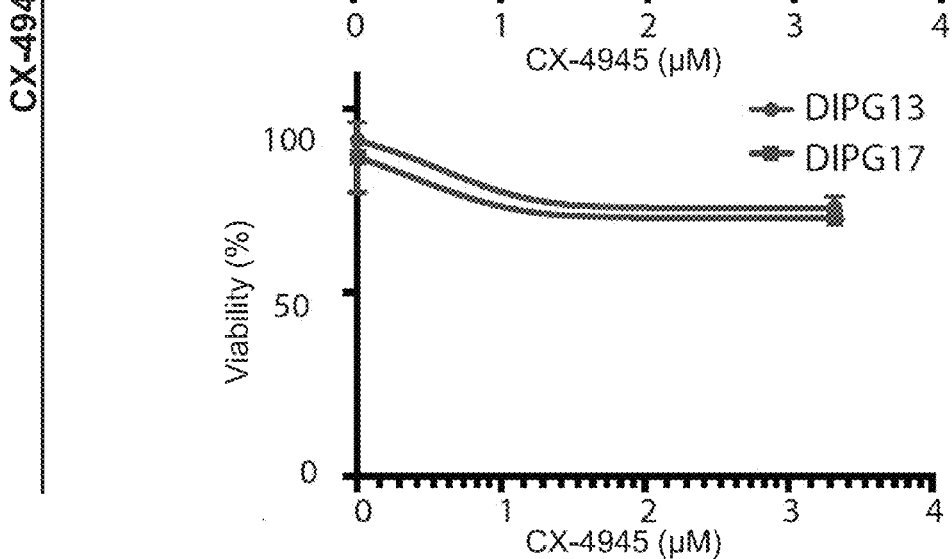
Figure 4A:
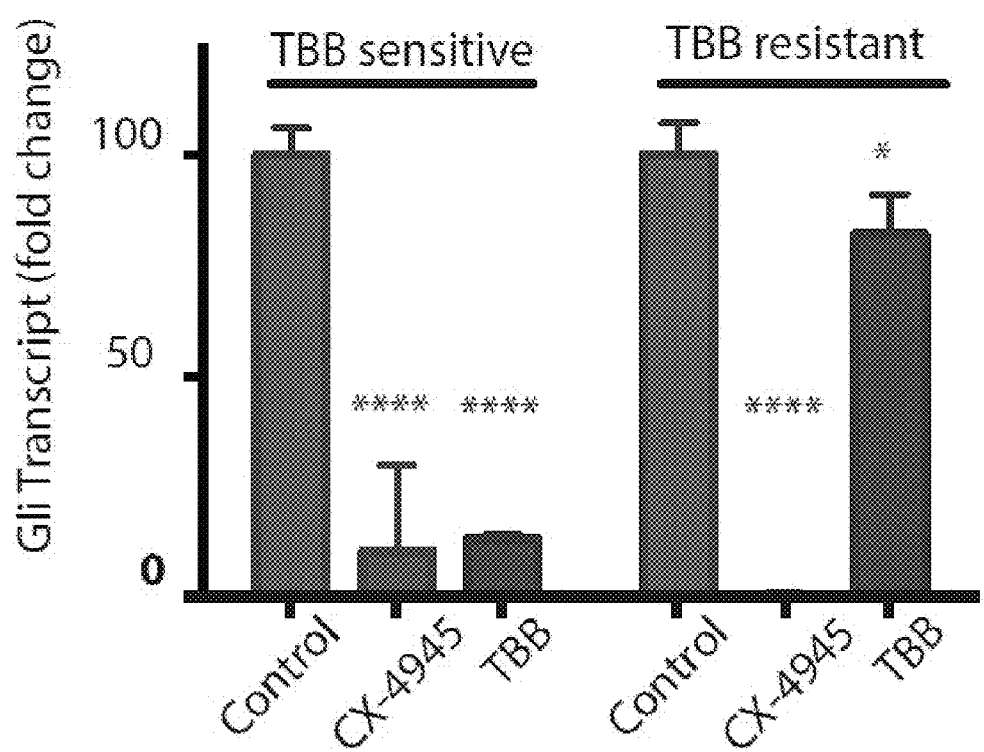
Figure 4B:
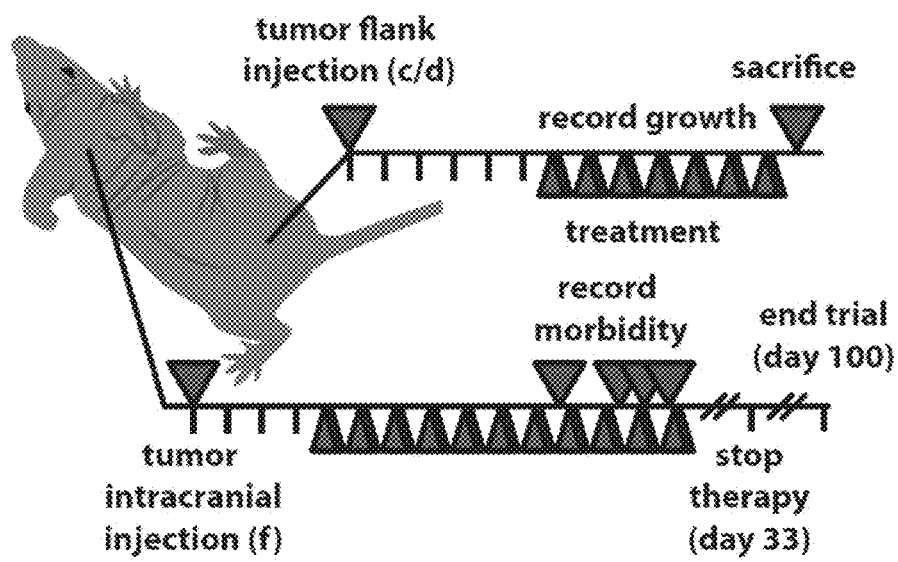
Figure 4C:
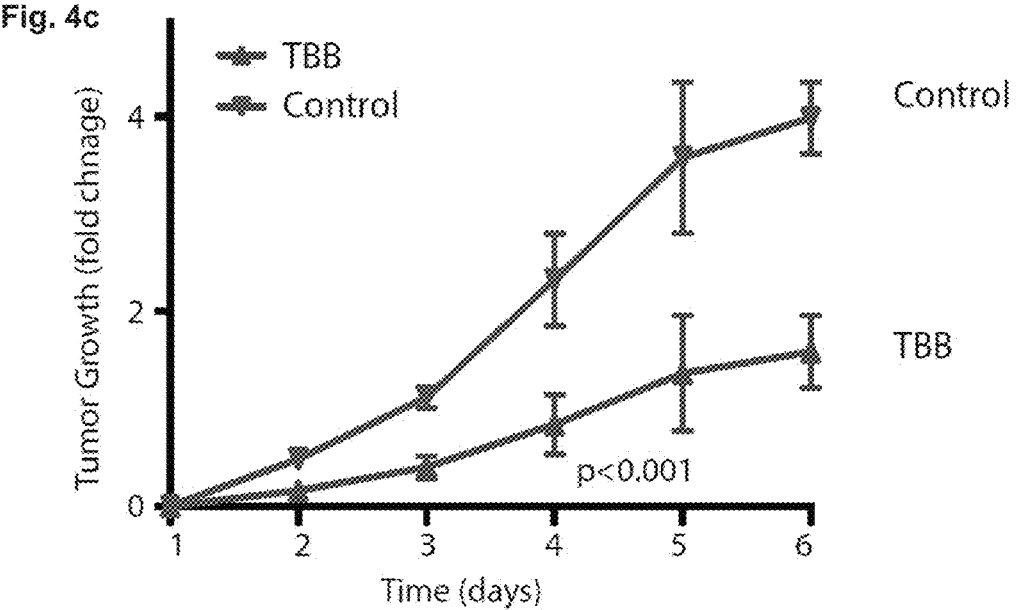
Figure 4D:
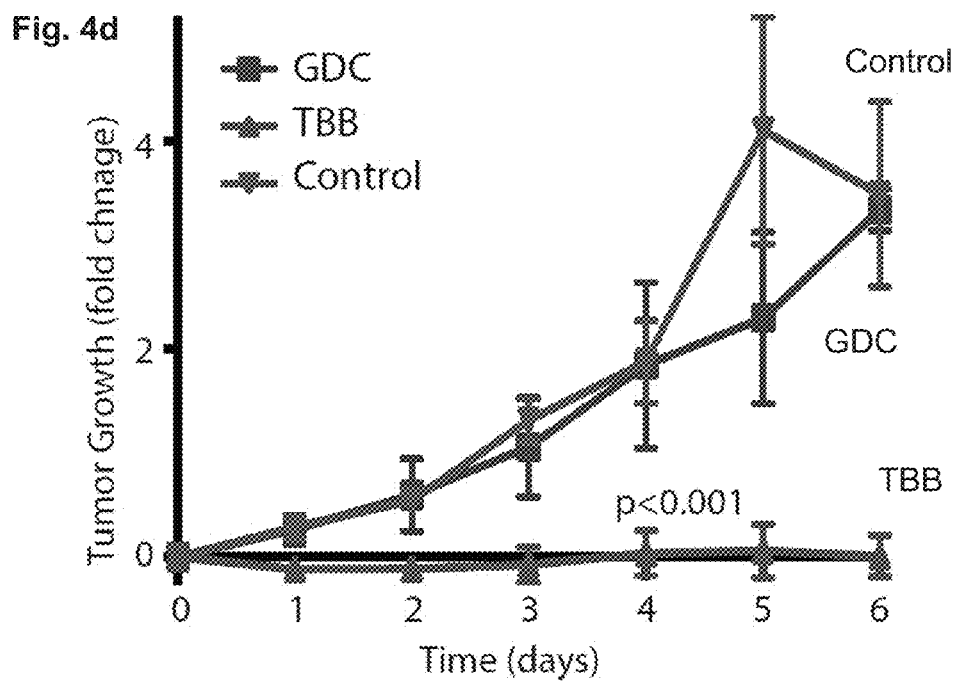
Figure 4E:
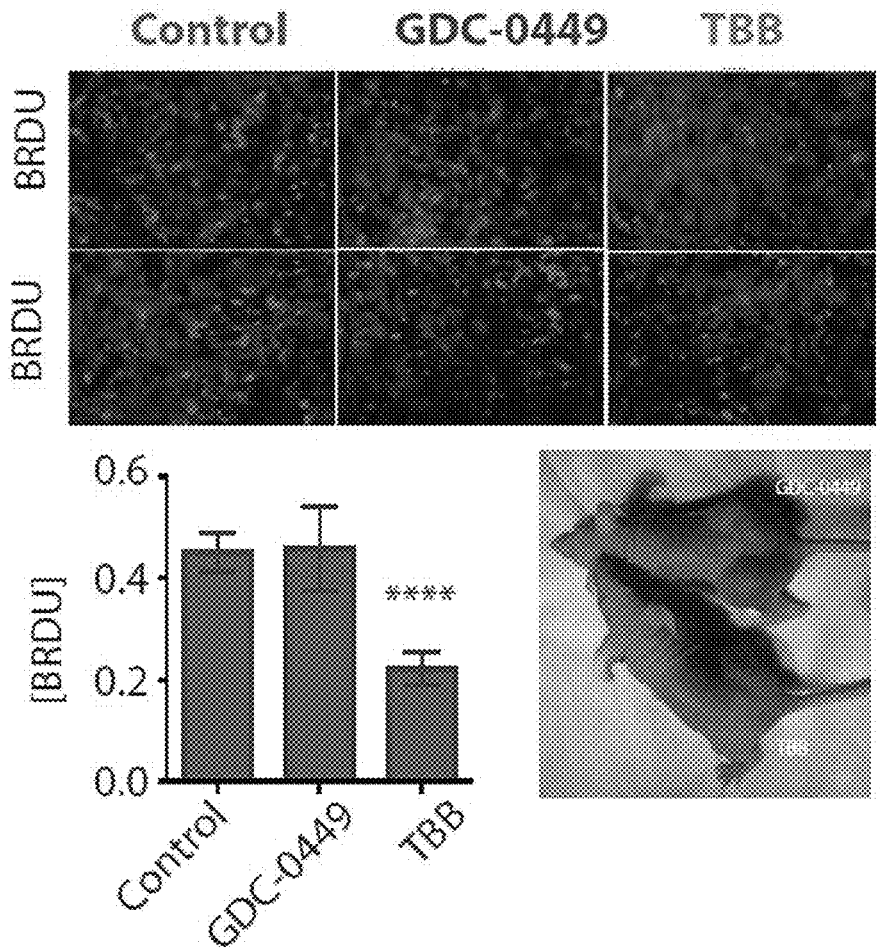
Figure 4F:
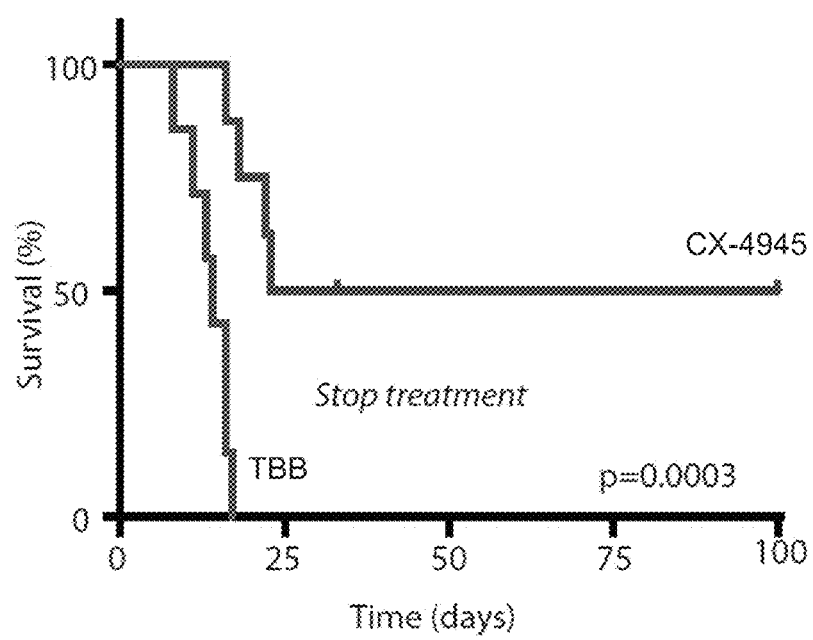
Figure 4G:
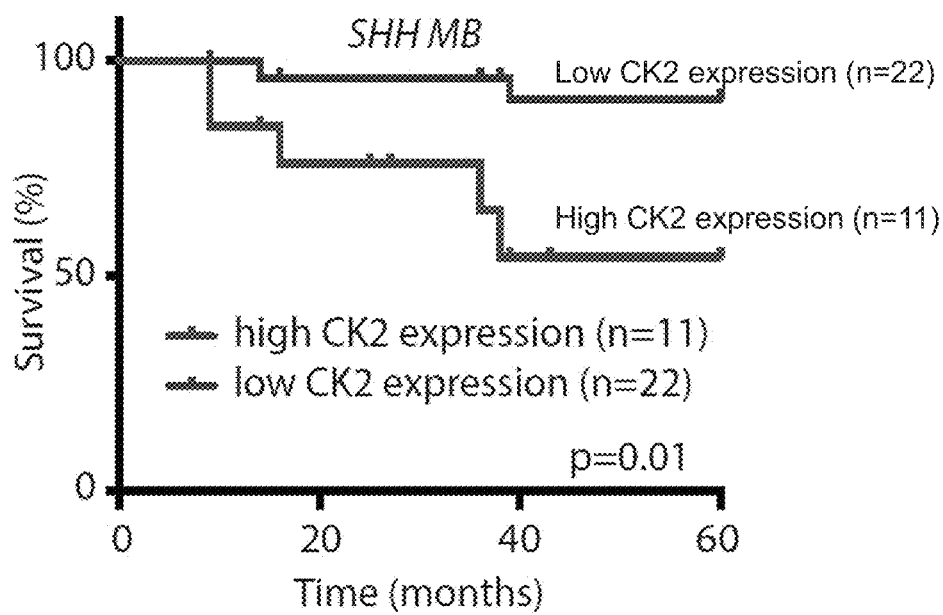

To identify the clinical significance of CK2 activity in Hh-driven MB, the effect of CK2 inhibitors on the growth of MB cells in vitro and in vivo was investigated. Both TBB and CX-4945 decreased cell viability in multiple MB cell lines derived from Ptch1+/− and Ptch1+/−; Trp53−/− mice (FIG. 4a). Furthermore, TBB administration (30 mg/kg IP BID) resulted in significant inhibition of MB flank allograft growth, as early as 3 days after initiating treatment (FIGS. 4b,c). To test efficacy of CK2 inhibitors against SMO inhibitor-resistant MBs, CX-4945 (75 mg/kg PO BID) was administered to mice harboring allografts of MB derived from Ptch+/−; Tpr53−/−; SmoD477G and Ptch+/−; Tpr53−/−; SmoD477G mice, which contain a point mutated Smo (SmoD477G) rendering them resistant to the only clinically available hedgehog inhibitor vismodegib (GDC-0449). Mice harboring flank allografts of these MB cells showed near-complete cessation of tumor growth in response to TBB (FIG. 4d) while a significant increase in survival was achieved with CX-4945 administration to mice harboring intracranial allografts of these same tumor cells (FIG. 4e). Previous work has shown that the most aggressive forms of human "SHH subtype" MBs harbor mutations rendering them resistant to SMO inhibitors. Therefore, the correlation of CSNK2A1 expression (in biopsy samples from children) with outcome in a cohort of SHH subgroup MB was next investigated. Kaplan-Meier survival analysis revealed patients with SHH-MB exhibiting low CK2 expression had a 90% overall survival rate at 60 months, while patients with high CK2 expression had a 53% survival (p=0.015) (FIG. 4g). No correlation between CK2 expression and survival was observed in other MB subgroups (Group 3/MYC, WNT), suggesting CK2 as a candidate biomarker and potential therapeutic target for patients with "hi-risk" SHH subgroup MB.

In conclusion, a novel developmental phosphoproteomics strategy was used to identify novel regulators of GNP proliferation and identified CK2 as a critical kinase that epigenetically modulates the Hh pathway through its regulation of Brd4. This work reinforces the interplay between signaling and the epigenome while providing substantial pre-clinical rationale to utilize CK2 inhibitors to treat human patients with MBs (e.g., Hh-driven MBs, including SMO inhibitor-resistant MBs) and potentially other Hh-driven cancers.

Materials and Methods
Mass Spectrometry
GNP Isolation.

Wildtype CD1-Elite mice (Charles River strain 482) were sacrificed at P1, P7 and P14. 35-40 mice were used per P1 and P14 biological replicate and 14-17 mice were used per P7 biological replicate. Cerebellum were dissected, meninges were removed and GNPs were isolated as previously described. Briefly, cerebellum were minced then placed in a digestion buffer consisting of 1×HBSS (ThermoFisher, NY, United States, 14,185), 10 U/ml papain (Worthington, N.J., United States, L5003126) and 250 U/ml DNase (Sigma, MO, United States, D4627). Papain solution was aspirated and replaced with 1×HBSS containing 8 mg/ml Ovomucoid (Worthington, N.J., United States, LK003182), 8 mg/ml bovine serum albumin (Sigma), and 250 U/ml DNase then titurated using a pasteur pipette to obtain a single-cell suspension. Cells were pelleted and resuspended in 0.02%

HBSS-BSA. Cells were passed through a 70 uM nylon cell strainer (VWR, 21,008-952) then underlaid with a step gradient of 35% and 65% Percoll (Sigma, P4937) and centrifuged at high speed for 12 min at room temperature. GNPs were carefully collected from the 35/65% interface and washed in PBS/BSA then centrifuged. Pellet was flash frozen in liquid nitrogen and kept at −80° C. until all samples were collected for mass spectrometry.

Sample Preparation for Quantitative Mass Spectrometry Analysis.

Sample were prepared as previously described[3] with the following modification. All solutions are reported as final concentrations. Lysis buffer (8M Urea, 1% SDS, 50 mM Tris pH 8.5, Protease and Phosphatase inhibitors from Roche) was added to the cell pellets to achieve a cell lysate with a protein concentration between 2-8 mg/mL. A micro-BCA assay (Pierce) was used to determine the final protein concentration in the cell lysate. Proteins were reduced and alkylated as previously described. Proteins were precipitated using methanol/chloroform. In brief, four volumes of methanol was added to the cell lysate, followed by one volume of chloroform, and finally three volumes of water. The mixture was vortexed and centrifuged to separate the chloroform phase from the aqueous phase. The precipitated protein was washed with one volume of ice cold methanol. The washed precipitated protein was allowed to air dry. Precipitated protein was resuspended in 4M Urea, 50 mM Tris pH 8.5. Proteins were first digested with LysC (1:50; enzyme:protein) for 12 hours at 25° C. The LysC digestion is diluted down to 1M Urea, 50 mM Tris pH8.5 and then digested with trypsin (1:100; enzyme:protein) for another 8 hours at 25° C. Peptides were desalted using a $C_{18}$ solid phase extraction cartridges as previously described. Dried peptides were resuspended in 200 mM EPPS, pH 8.0. Peptide quantification was performed using the micro-BCA assay (Pierce). The same amount of peptide from each condition was labeled with tandem mass tag (TMT) reagent (1:4; peptide: TMT label) (Pierce). The 6-plex and 10-plex labeling reactions were performed for 2 hours at 25° C. Modification of tyrosine residue with TMT was reversed by the addition of 5% hydroxyl amine for 15 minutes at 25° C. The reaction was quenched with 0.5% TFA and samples were combined at a 1:1:1:1:1:1 ratio for 6-plex experiments or 1:1:1:1:1:1: 1:1:1:1 for 10-plex experiments. Combined samples were desalted and offline fractionated into 24 fractions as previously described.

Liquid Chromatography-MS3 Spectrometry.

12 of the 24 peptide fraction from the basic reverse phase step (every other fraction) were analyzed with an LC-MS3 data collection strategy on an Orbitrap Fusion mass spectrometer (Thermo Fisher Scientific) equipped with a Proxeon Easy nLC 1000 for online sample handling and peptide separations. Approximately 5 µg of peptide resuspended in 5% formic acid+5% acetonitrile was loaded onto a 100 µm inner diameter fused-silica micro capillary with a needle tip pulled to an internal diameter less than 5 µm. The column was packed in-house to a length of 35 cm with a $C_{18}$ reverse phase resin (GP118 resin 1.8 µm, 120 Å, Sepax Technologies). The peptides were separated using a 120 min linear gradient from 3% to 25% buffer B (100% ACN+ 0.125% formic acid) equilibrated with buffer A (3% ACN+ 0.125% formic acid) at a flow rate of 600 nL/min across the column. The scan sequence for the Fusion Orbitrap began with an MS1 spectrum (Orbitrap analysis, resolution 120, 000, 400-1400 m/z scan range, AGC target $2 \times 10^5$, maximum injection time 100 ms, dynamic exclusion of 75 seconds). 'Top speed' (1 second) was selected for MS2 analysis, which consisted of CID (quadrupole isolation set at 0.5 Da and ion trap analysis, AGC $4 \times 10^3$, NCE 35, maximum injection time 150 ms). The top ten precursors from each MS2 scan were selected for MS3 analysis (synchronous precursor selection), in which precursors were fragmented by HCD prior to Orbitrap analysis (NCE 55, max AGC $5 \times 10^4$, maximum injection time 150 ms, isolation window 2.5 Da, resolution 60,000 (10-plex experiments) or 15,000 (6-plex experiments))

LC-MS3 Data Analysis.

A suite of in-house software tools were used for .RAW file processing and controlling peptide and protein level false discovery rates, assembling proteins from peptides, and protein quantification from peptides as previously described. MS/MS spectra were searched against a Uniprot human database (February 2014) with both the forward and reverse sequences. Database search criteria are as follows: tryptic with two missed cleavages, a precursor mass tolerance of 50 ppm, fragment ion mass tolerance of 1.0 Da, static alkylation of cysteine (57.02146 Da), static TMT labeling of lysine residues and N-termini of peptides (229.162932 Da), and variable oxidation of methionine (15.99491 Da). TMT reporter ion intensities were measured using a 0.03 Da window (6-plex) or 0.003 Da window (10-plex) around the theoretical m/z for each reporter ion in the MS3 scan. Peptide spectral matches with poor quality MS3 spectra were excluded from quantitation (<100 summed signal-to-noise across 6 channels and <0.5 precursor isolation specificity for 6-plexes or (<200 summed signal-to-noise across 10 channels and <0.5 precursor isolation specificity for 10-plexes).

Sample Comparison.

Each biological replicate was median-adjusted to 10 to account for differences in sample loading, resulting in the following changes in the proteomic dataset: P1A:−0.0362, P1B:−0.0879, P1C:+0.20476, P7A:+0.03374, P7B:−0.2761, P7C:−0.2865, P14A:+0.78605, P14B+0.65244, P14C:+ 0.71771, MB:+0.04692 and the following changes for the phosphoproteomic dataset: P1A: −0.040163003, P1B:− 0.124877212, P1C:−0.009654128, P7A:−0.170361415, P7B:−0.341821765, P7C:−0.117111143, P14A:+ 1.114888992, P14B:+1.060676918, P14C:+0.955615374, MB:+0.43299154. Log 2 transformed P1:P7 and P7:P14 ratios were determined and phosphopeptide changes were normalized to protein changes. Values outside of 1.5SD were considered 'significant changers".

Gene Set Enrichment Analysis (GSEA) of significantly changing peptides was performed using the JavaGSEA application provided by the Broad Institute "http" followed by "s://w" followed by "ww.broadinstitute." followed by "org/gsea/in" followed by "dex.jsp" as previously described and biological processes with a Bonferroni-corrected p<0.005 were considered significant. Differentially expressed terms were visualized using the GENE-E desktop application "http" followed by "://www.broa" followed by "dinstitute.or" followed by "g/cancer/software/GENE-E/" and heierarchical clustering was performed using Pearson correlation and average linkage metric across samples and proteins.

Motif analysis of significantly changing phosphopeptides was performed using Motif-X as previously described. Briefly, Motif-X is an iterative statistical approach to identifying protein phosphorylation motifs in large-scale phosphoproteomic data sets built on a greedy recursive search of the sequence space to identify highly correlated residue/ position pairs with the lowest P values. In this study a binomial probability threshold of $p<10^{-6}$ and occurrence threshold of 20 was used.

CK2 Inhibition in Developing Mouse

Math1/nGFPtransgenic mice[8] were treated with DMSO or TBB (30 mg/kg IP bid) (EMD 218697) from P4-P7 then sacrificed 6 h following their final treatment. Brains were dissected, fixed in 4% PFA overnight then transferred into 20% sucrose for 24 h. Sections were mounted in O.C.T and sectioned at 20 μm then air-dried for 20 min prior to storing at −20° C. for up to 2 months. Sections were blocked in 0.2% triton X-100 and 2% goat serum diluted in sterile PBS for 1 h at RT. Primary antibodies used were: anti-NeuN Ab (1:200, COT: 2459079, EMD Millipore), anti-Tag1 Ab (1:100, antibody derived in the Scott lab) and TUNEL staining as per manufacturers instructions (Roche In situ Cell Death Detection Kit, cat. no. 1 684 809). All sections were incubated in primary antibody overnight at 4° C. and counter-stained with Hoechst33258 (final concentration 1 μl/ml in PBS) at RT for 10 min. Images were taken on a Leica TCS SP8 confocal microscope. Images were randomized and all measurements (length, width, Atoh-1, Tag1, TUNNEL staining) were performed by a blinded collaborator. Cerebellar folia length was compared between matched sections of control and treated mice by measuring the maximal length from the mid-base to the tip of the culmun (lobule 4/5). Culmen width was measured 600 uM from the base of the folia between lobules 5 and 6. Prism statistical analysis software was used (GraphPad Software, CA) to calculate significance as determined by two-tailed T-tests.

Epistasis Studies

Reagents and Cell Lines.

Sufu$^{-/-}$ MEFs (conditional deletion of exons 4-8) were kindly provided by Pao-Tien Chang (UCSF). SAG (S7779), GDC-0449 (Vismodegib, S1082) and CX-4945 (Silmitasertib, S2248) was purchased from SelleckChem.com. TBB was purchased from EMD (218697). Shh-N conditional medium was made using a HEK 293 cell line that stably secretes ShhN as previously described. Myc-GL12-DN (17649, pCS2-MT-GLI2-deltaN) plasmid was purchased from Addgene (Cambridge, Mass., USA). Plasmid transfection was performed using Turbofect transfection reagent (#R0531, Thermo Scientific) according to the manufacturers instructions starting by plating NIH3T3's in a 6 well dish at 400,000 cells/well. Pooled custom Dharmacon ON-TARGET plus specificity enhanced siRNA were created against csnk2a1, csnk2a2 and csnk2b. siRNA sequences were kindly provided by Dr. David Seldin, (Boston University School of Medicine) and are listed in Supplementary Table 5. All pools were validated for knockdown efficiency and specificity. Scramble siRNA was purchased from Dharmacon (D-001810-01-05).

RT-qPCR.

NIH3T3s or SUFU−/− MEFs were plated in 6 well plates at 400,000 cells/well in 10% FBS media constituted of DMEM (Invitrogen11960-069) supplemented with 10% FBS (Hyclone Labs SH30070.02), pen/strep (Life Technologies 15140-122), sodium pyruvate (Invitrogen 11360-070) and glutamax (Invitrogen 35050-061). Cells were then starved in 0.5% FBS for 24 h prior to treatment with 25% ShhN conditioned media in 0.5% FBS+/− drug treatment. GliΔN were treated 48 h post transfection. Unless otherwise stated, all treatments were performed for 6 h. Cell lysis and RNA extraction was performed using Qiashredder homogenizers (Qiagen 79654) and RNEasy mini kits (qiagen 74104) as per manufacturer's instructions. RNA was quantified on a nanodrop spectrophotometer (nanoddrop technologies ND-2000C). Transcript quantification was performed using a TaqMan RNA-to-Ct 1-Step Kit (Life technologies, 4392656) and the Applied Biosystems 7500 RT-PCR system as per the manufacturer's instructions. All primers were commercially available TaqMan® Gene Expression Assay probes purchased from Life Technologies (csnk2a1: Mm00786779_s1, csnk2a2: Mm01243455_m1, csnk2b: Mm00487216_m1, Gli1: Mm00494654_m1, Gli2: Mm.273292, Ccnd1: Mm.273049, Ptch: Mm00436047_m1).

Gli2 Stability.

Gli2ΔN cells were lysed with RIPA buffer (sc-24948, Santa Cruz Biotechnology) supplemented with Halt Protease & Phosphatase Inhibitor (Thermo #1861218) for 30 min on ice and lysates were cleared by centrifugation at 13000 rpm, 15 min at 4° C. Supernatants were incubated with 6× Lamelli sample buffer (10570021-1, BioWorld) at 95° C. for 5 min. The samples were then separated with a 7% SDS-PAGE gel and immunoblotted with anti-Gli2 (AF3635-SP, R&D) and anti-β-tubulin (ab6046, Abcam).

Brd4, H3K27ac, Gli2 Chromatin Immunoprecipitation

Sample Preparation.

Wildtype CD1-Elite (Charles River strain 482) P7 mice were randomized to control or treatment groups then given two injections of DMSO (control) or TBB (30 mg/kg) q12h×2. Mice were sacrificed and GNPs were isolated as described in "GNP isolation". Chomatin immunoprecipitation was performed as previously described. GNPs were cross-linked in 1% formaldehyde for 10 minutes at RT then fixation was stopped by adding 2.5M glycine for 10 minutes. Samples were washed and stored at −80 until all samples were collected. Crosslinked cells were later thawed on ice, incubated in chilled RIPA for 10 min and sonicated 7×15 min. To prepare blocking beads, 60 uL/sample of protein G beads (Roche 11719416001) were incubated with 5% BSA on a rocker at 4 degrees for at least 1 h. Pelleted samples were then transferred to a chilled tube containing blocking beads and rocked end over end for 1 hour at 4° C. Sonicated chromatin was then left in Brd4 (AF3526-SP, R&D), H3K27ac (ab4729, abcam), Gli2 (AF3526-SP, R&D) or IGG (12-370, EMD) antibody overnight. Protein G beads were then added to samples and rocked for 1 h. Samples were pelleted and washed at 4 degrees with wash buffers 1-4 for 5 minutes each (Wash Buffer I: 20 mM Tris-HCl, pH 8.0, 0.1% SDS, 1% Triton X-100, 2 mM EDTA, 150 mM NaCl, Wash Buffer II: Wash Buffer I, with 500 mM NaCl, Wash Buffer III: 10 mM Tris, pH 8.0, 0.25M LiCl, 1% Igepal CA-630 (NP-40), 1% Na-Deoxycholate, 1 mM EDTA, Wash Buffer IV: (TE buffer) 10 mM Tris-HCl, pH 8.0, 1 mM EDTA). After the final wash, buffer was removed and TES was added. Samples were eluted at by heating to 65° for 10 minutes, vortexing for 5 seconds every 2 minutes. Proteinase K/Glycogen was added and samples were incubated overnight at 65°. DNA was purified via phenol-chloroform extraction and ethanol precipitation then treated with RNAse A for 1 h. Final product was cleaned up using a qiagen PCR cleanup kit. ChIP and input DNA was quantified using Qubit DS DNA HS assay as per manufacturer's protocol (ThermoFisher Q32851). Library prep was performed using the NEBNext® Ultra™ ChIP-Seq Library Prep Master Mix Set for Illumine® (E6240S/L) as per manufacturers protocol. Library was quantified via Qubit DS DNA HS assay and library quality was determined using an Agilent 2100 Bioanalyzer. Equal amounts of each library were pooled for 36 bp single end sequencing. For Brd4 Chip-qPCR experiments, qPCR was performed using 2× Maxima SYBR Green qPCR Master Mix (#K0251, Thermo Scientific) on an Eppendorf Mastercycler PCR machine. All qPCR results were normalized to IGG control (Ab:X) ChIP performed in parallel to the Brd4 ChIP. ChIP-qPCR primer sequences are listed in supplementary table 5 and validated for single amplification product prior to use.

In Vitro Medulloblastoma Studies

Cell Viability.

Ptch+/−MB cell lines MB55 and MB21 were kindly gifted from Dr. Rosalind Segal (Dana Farber Cancer Institute, Harvard Medical School) and Ptch$^{+/-}$; p53$^{-/-}$ MB53 cells were kindly gifted from Charles Rudin (Memorial Sloan-Kettering Cancer Center). All cell lines were validated for high Gli activity. Cell viability was assessed using CellTiter-Glo (G7573, Promega, WI, USA) according to the manufacturers instructions. Cells were plated at 10000 cells/well in 96-well plates, treated with drugs as indicated and data was collected on a TECAN Infinite 200 plate reader.

Acquired Resistance.

Medulloblastoma cell lines (MB53, MB55 and MB21 cells) were cultured in Neurobasal (Life Technologies 10888-022)+B27 supplement (Invitrogen 17504044)+DMSO (0.1%), CX-4945 (10 uM) or TBB (50 uM). Surviving cells were passaged for 2 weeks after which only control treated (DMSO) and MB55 TBB treated (50 uM) cells remained. cDNA from the three control lines and MB55 TBB resistant lines were synthesized using the ABI High-Capacity cDNA Reverse Transcription Kit (thermo 4368814) and amplified using the Q5® High-Fidelity DNA Polymerase (NEB M0491) as per the manufacturer's protocol. Primer sequences are provided in supplemental table 5.

In Silico Analysis of Mutant Vs Wildtype Binding of TBB and CX-4945

All the crystal structures of CK2 were retrieved from the PDB (Protein Data Bank). In particular to perform docking and molecular dynamics simulations, the crystal structure of human CK2 in complex with CX4945 was used (PDB code: 3PE1). However, to compare the binding motif of TBB and to evaluate its position in the structure 3PE1, the crystallographic complex TBB/CK2 Zea mays was also considered (PDB code: 1J91). The crystal structures were processed in order to remove unwanted ligands and water molecules. Hydrogen atoms were added to the protein structure using standard geometries. To minimize contacts between hydrogens, the structures were subjected to Amber99 force-field minimization until the rms (root mean square) of conjugate gradient was <0.1 kcal·mol$^{-1}$·Å$^{-1}$ (1 Å=0.1 nm) keeping the heavy atoms fixed at their crystallographic positions. A similar protocol were used also to minimize the structures subjected to in silico mutagenesis. To strictly calibrate the high-throughput docking protocol, a small database of known CK2 inhibitors was built and a set of docking runs was performed. After the calibration phase, TBB and CX4945 were docked directly into the ATP binding site of selected CK2 crystal structures, by using AUTODOCK software[12]. Molecular dynamics (MD) simulations of the considered structures (parameterized with AMBER99) were performed with NAMD 2.8 in order to verify their stability over time; in particular a 100 ns of NPT (1 atm, 300K) MD simulation were performed after an equilibration phase of 1 ns (positional restraints were applied on carbon atoms to equilibrate the solvent around the protein).

In Vivo Mouse Studies

Flank Studies.

In vivo efficacy studies were performed in accordance with protocols approved by the Institutional Animal Care and Use Committee at Stanford University. SmoWT-MB and SmoD477G-MB cells isolated from either parental SmoWT or SmoD477G mouse Ptch$^{+/-}$; p53$^{-/-}$ MB hindflank allografts were kindly provided by Charles Rudin (Memorial Sloan-Kettering Cancer Center). Ptch+/−; Tpr53−/−, or, Ptch+/−; Tpr53−/−; SmoD477G MB cells were mixed 1:1 with matrigel and 10$^7$ cells were injected into both flanks of a Nu/Nu mouse. Once tumors reached 225-275 mm$^3$, mice were randomized to treatment vs. control groups. Treatment groups received 30 mg/kg IP BID of TBB (reconstituted in DMSO at 50 ug/uL), or 37.5 mg/kg IP BID of GDC-0449 (reconstituted in DMSO at 62.5 ug/uL). Control mice were treated with an equivalent volume of DMSO. Corn oil was used in all groups to a total volume of 180 uL/injection and all doses were given with a 28 g insulin syringe. Tumors were measured and mice were weighed daily. Once tumors reached 1.5 cm$^2$ or met institutional euthanasia criteria, mice were sacrificed and tumors were harvested. Growth curves were generated using GraphPad Prism and significance was measured by two-way ANOVA.

Intracranial Xenografts.

Ptch+/−; Tpr53−/−; SmoD477G were suspended in sterile PBS to an adjusted final volume of at 80,000 cells/2 uL injection. Mice were anesthetized and fixed to a stereotactic frame and the head was sterilized. A small sagittal incision was made in the mouse's scalp to expose the area surrounding lambda. The skull was sterilized a 0.7 mm drill bit was used to create a midline hole located 2 mm down from lambda. A Hamilton syringe with affixed 26 g needle was lowered to a depth of ~3 mm then withdraw to 2.75 mm before injecting 2 uL (80,000) cells at 0.5 ul/min. The drill hole was closed with a thin slip of bone wax and the wound was closed. Mice were randomized and a blinded collaborator began treatment at 48 h with either CX-4945 (37.5 mg/kg PO BID, reconstituted in DMSO) or DMSO (equivalent volume to treatment group, dosed IP BID). Corn oil was used as vehicle for both CX-4945 and DMSO. Weight, morbidity and survival were measured by a blinded collaborator. Kaplan-meyer survival curves were generated using GraphPad Prism and significance was measured by Logrank Mantel-Cox test.

What is claimed is:

1. A method of treating an individual who has a medulloblastoma tumor, the method comprising:
    administering a composition to an individual who has a medulloblastoma tumor, at a dose sufficient to reduce the size and/or growth rate of the medulloblastoma tumor, wherein the composition comprises the casein kinase II (CK2) inhibitor 5-(3-Chloroanilino)benzo[c][2,6]naphthyridine-8-carboxylic acid (CX-4945).

2. The method according to claim 1, wherein the medulloblastoma tumor is a hedgehog-dependent medulloblastoma tumor.

3. The method according to claim 1, wherein the medulloblastoma tumor is a hedgehog-independent medulloblastoma tumor.

4. The method according to claim 1, wherein the medulloblastoma tumor is resistant to smoothened (SMO) inhibitor, vismodegib (GDC-0449).

5. The method according to claim 1, wherein the medulloblastoma is resistant to 4,5,6,7-tetrabromo-2H-benzotriazole (TBB).

6. The method according to claim 1, wherein said administering comprises local administration.

7. The method according to claim 1, wherein said administering comprises systemic administration.

8. The method according to claim 7, wherein said systemic administration comprises oral administration.

9. The method according to claim 1, further comprising a step of measuring an expression level of Gli1 RNA in a biological sample from the individual.

10. The method according to claim 9, wherein the biological sample is a biopsy from the medulloblastoma tumor.

11. The method according to claim 1, further comprising a step of measuring an expression level of CSNK2A1 RNA in a biological sample from the individual.

12. The method according to claim 11, wherein the biological sample is a biopsy from the medulloblastoma tumor.

13. The method according to claim 1, wherein the dose is sufficient to cause long term regression of the medulloblastoma tumor.

14. The method according to claim 1, wherein the dose is sufficient to increase the chance of survival of the individual.

* * * * *

SEQUENCE LISTING

<160> NUMBER OF SEQ ID NOS: 22

<210> SEQ ID NO 1
<211> LENGTH: 13
<212> TYPE: PRT
<213> ORGANISM: Artificial sequence
<220> FEATURE:
<223> OTHER INFORMATION: Synthetic sequence

<400> SEQUENCE: 1

```
Asp Asn Lys Asp Asp Asp Ser Asp Pro Glu Thr Ala Asn
1               5                   10
```

<210> SEQ ID NO 2
<211> LENGTH: 13
<212> TYPE: PRT
<213> ORGANISM: Artificial sequence
<220> FEATURE:
<223> OTHER INFORMATION: Synthetic sequence

<400> SEQUENCE: 2

```
Pro Gln Lys Gly Pro Ala Ser Asp Ser Glu Ala Glu Asp
1               5                   10
```

<210> SEQ ID NO 3
<211> LENGTH: 13
<212> TYPE: PRT
<213> ORGANISM: Artificial sequence
<220> FEATURE:
<223> OTHER INFORMATION: Synthetic sequence

<400> SEQUENCE: 3

```
His Gly Glu Asp Glu Asp Ser Asp Asn Glu Asp Asn Lys
1               5                   10
```

<210> SEQ ID NO 4
<211> LENGTH: 13
<212> TYPE: PRT
<213> ORGANISM: Artificial sequence
<220> FEATURE:
<223> OTHER INFORMATION: Synthetic sequence

<400> SEQUENCE: 4

```
Lys Gln Ser Asn Ala Ser Ser Asp Val Glu Val Glu Glu
1               5                   10
```

<210> SEQ ID NO 5
<211> LENGTH: 13
<212> TYPE: PRT
<213> ORGANISM: Artificial sequence
<220> FEATURE:
<223> OTHER INFORMATION: Synthetic sequence

<400> SEQUENCE: 5

```
Lys Arg Gln Leu Leu Asp Ser Asp Glu Glu Glu Asp Asp
1               5                   10
```

<210> SEQ ID NO 6
<211> LENGTH: 13
<212> TYPE: PRT
<213> ORGANISM: Artificial sequence
<220> FEATURE:
<223> OTHER INFORMATION: Synthetic sequence

<400> SEQUENCE: 6

```
Pro Thr Ser Glu Cys Val Ser Asp Val Glu Pro Asp Thr
1               5                   10
```

<210> SEQ ID NO 7
<211> LENGTH: 13
<212> TYPE: PRT
<213> ORGANISM: Artificial sequence
<220> FEATURE:
<223> OTHER INFORMATION: Synthetic sequence

<400> SEQUENCE: 7

```
Glu Glu Lys Leu Gly Thr Ser Asp Gly Glu Glu Glu Arg
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic sequence

<400> SEQUENCE: 8

Gly Asp Asp Asp Glu Glu Ser Asp Glu Glu Ala Val Lys
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic sequence

<400> SEQUENCE: 9

Gly Val Gln Ala Gly Asn Ser Asp Thr Glu Gly Gly Gln
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic sequence

<400> SEQUENCE: 10

Thr Lys Arg Lys Ser Leu Ser Asp Ser Glu Ser Asp Asp
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetic sequence

<400> SEQUENCE: 11

Glu Met Trp Asn Asn Leu Ser Asp Asn Glu Lys Gln Pro
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic sequence

<400> SEQUENCE: 12

Ser Ala Leu Leu Phe Ser Ser Asp Glu Glu Asp Gln Trp
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic sequence

<400> SEQUENCE: 13

Glu Asp Glu Asn Asp Ala Ser Asp Asp Glu Asp Asp Asp
```

```
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic sequence

<400> SEQUENCE: 14

Ala Ser Arg Val Pro Ser Ser Asp Glu Glu Val Val Glu
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthetic sequence

<400> SEQUENCE: 15

Arg Asp Pro Lys Pro Asp Ser Asp Thr Glu Lys Tyr Pro
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic sequence

<400> SEQUENCE: 16

Glu Lys Leu Asp Gly Glu Ser Asp Lys Glu Gln Phe Asp
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic sequence

<400> SEQUENCE: 17

His Glu Asp Gly Thr Gln Ser Asp Ser Glu Asp Pro Leu
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic sequence

<400> SEQUENCE: 18

Arg Lys Ala Ala Val Leu Ser Asp Ser Glu Asp Asp Ala
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic sequence

<400> SEQUENCE: 19

Met Thr Glu Asp Ile Arg Ser Asp Val Glu Glu Pro Asp
1               5                   10
```

```
<210> SEQ ID NO 20
<211> LENGTH: 13
<212> TYPE: PRT
<213> ORGANISM: Artificial sequence
<220> FEATURE:
<223> OTHER INFORMATION: Synthetic sequence

<400> SEQUENCE: 20

Asp Asp Gly Thr Asn Asp Ser Asp Leu Glu Lys Gly Ala
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic sequence

<400> SEQUENCE: 21

Val Gly Arg Ala Gly Asp Ser Asp Glu Glu Ser Arg Thr
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic sequence

<400> SEQUENCE: 22

Ser Lys Tyr Tyr Ser Asp Ser Asp Asp Glu Leu Thr Val
1               5                   10
```